(12) United States Patent
Vallius et al.

(10) Patent No.: US 12,431,971 B2
(45) Date of Patent: Sep. 30, 2025

(54) CONFIGURABLE PHOTOPLETHYSMOGRAM SYSTEM

(71) Applicant: Oura Health Oy, Oulu (FI)

(72) Inventors: Tero Juhani Vallius, Kontio (FI); Olli Petteri Heikkinen, Oulu (FI); Jussi Petteri Järvelä, Kempele (FI); Heikki Juhani Huttunen, Haukipudas (FI); Teemu Juhani Haverinen, Oulu (FI); Antti Aleksi Rantanen, Oulu (FI); Sami Seppo Pelkonen, Oulu (FI); Juha-Pekka Syrjälä, Oulu (FI); Markku Olavi Koskela, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/768,232

(22) Filed: Jul. 10, 2024

(65) Prior Publication Data
US 2024/0364420 A1    Oct. 31, 2024

Related U.S. Application Data

(63) Continuation of application No. 17/963,561, filed on Oct. 11, 2022, now Pat. No. 12,074,637.

(60) Provisional application No. 63/255,140, filed on Oct. 13, 2021.

(51) Int. Cl.
*H04B 10/00* (2013.01)
*H04B 10/079* (2013.01)
*H04J 14/00* (2006.01)

(52) U.S. Cl.
CPC .............. *H04B 10/07953* (2013.01)

(58) Field of Classification Search
CPC ............ A61B 5/02416; A61B 5/02427; A61B 5/02433; A61B 5/02438; A61B 5/02444
See application file for complete search history.

(56) References Cited

U.S. PATENT DOCUMENTS

| | | | | |
|---|---|---|---|---|
| 10,568,525 B1 * | 2/2020 | Wu | ...................... | A61B 5/6824 |
| 11,781,907 B2 | 10/2023 | Capella et al. | | |
| 2017/0311825 A1 | 11/2017 | Weekly et al. | | |
| 2019/0082985 A1 * | 3/2019 | Hong | ................. | A61B 5/02427 |

* cited by examiner

*Primary Examiner* — Daniel G Dobson
(74) *Attorney, Agent, or Firm* — Holland & Hart LLP

(57) ABSTRACT

Methods, systems, and devices for optical signal measurement are described. A wearable electronic device may activate a first combination of optical sensors, the first combination of optical sensors including a set of transmitter sensors and a set of receiver sensors. In some cases, one or more optical sensor of the first combination of optical sensors may be positioned under a protrusion on an inner surface of the wearable electronic device. The device may measure, at the set of receiver sensors at a first time, one or more signals from the set of transmitter sensors, determine a signal quality metric associated with the one or more signals, and select a second combination of optical sensors for use at a second time based on the signal quality metric.

20 Claims, 16 Drawing Sheets

CONFIGURABLE PHOTOPLETHYSMOGRAM SYSTEM

CROSS REFERENCE

The present Application for Patent is a continuation of U.S. patent application Ser. No. 17/963,561 by Vallius et al., entitled "CONFIGURABLE PHOTOPLETHYSMOGRAM SYSTEM," filed Oct. 11, 2022, which claims the benefit of U.S. Provisional Patent Application No. 63/255,140 by VALLIUS et al., entitled "CONFIGURABLE PHOTOPLETHYSMOGRAM SYSTEM," filed Oct. 13, 2021, each of which is assigned to the assignee hereof, and each of which is expressly incorporated by reference herein.

FIELD OF TECHNOLOGY

The following relates to wearable devices and data processing, including a configurable photoplethysmogram (PPG) system.

BACKGROUND

Some wearable devices may be configured to collect data from the wearer using a PPG signal. The PPG signal may be used to derive a number of other physiological parameters such as heart rate, heart rate variability, and the like. However, existing techniques for collecting PPG data using sensors of a wearable device may be improved.

DETAILED DESCRIPTION

Figure 1:
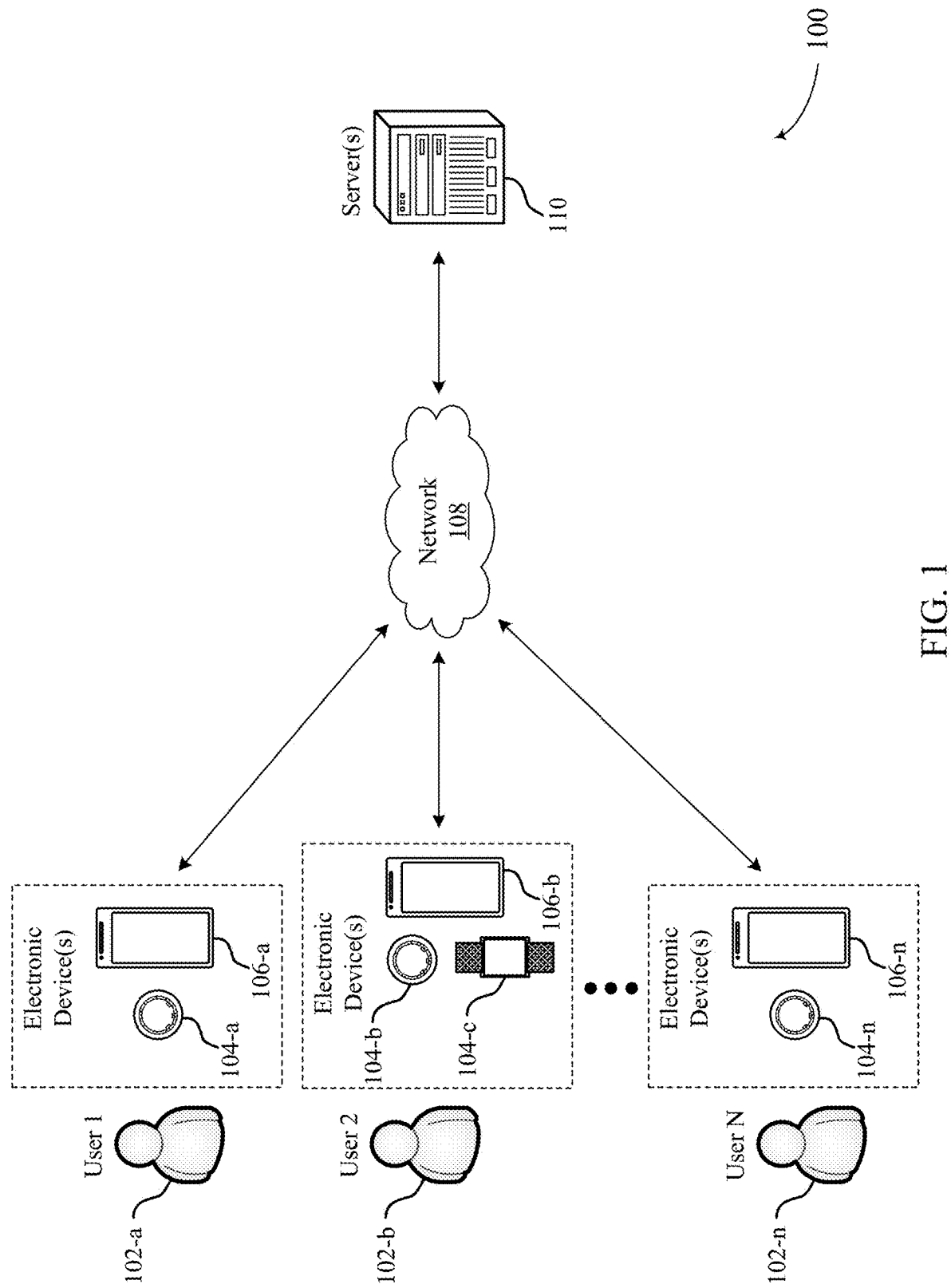
FIGS. 1 and 2 illustrate examples of systems that support a configurable PPG system in accordance with aspects of the present disclosure.

A wearable electronic device, such as a wearable electronic ring (e.g., a ring) may include a PPG system that measures a user's pulse waveform. The PPG system may include one or more optical transmitters and one or more optical receivers. In some examples, the optical transmitters (e.g., light-emitting diodes (LEDs)) may transmit one or more wavelengths of light, such as infrared (IR), red, yellow, blue, and/or green wavelengths. Some devices may include two or more optical transmitters that are configured to transmit light based on a trigger (e.g., configured periodicity, lack of motion, etc.). However, there may be several factors that impact the quality of the measured signal from the activated optical transmitters (e.g., motion, position of the wearable against the skin, ambient light, etc.). As such, techniques for selecting optical transmitters and optical receivers to activate based on a measured signal quality or other quality metrics may be desired to increase the accuracy of measured signals.

In accordance with aspects of the present disclosure, the PPG system may select the transmitters and receivers used to measure a user's pulse waveform. For example, the PPG system may select a transmitter-receiver combination based on a variety of factors, such as signal strength, signal quality, user movement, time of day, temperature (e.g., ambient temperature, skin temperature), motion (e.g., acceleration), power consumption, etc. As another example, the PPG system may select different transmitter wavelengths based on other considerations, such as ambient light.

The PPG system may transition between different transmitter-receiver combinations and wavelengths over time based on changing circumstances. The different configurable PPG transmitter/receiver arrangements may help ensure that the ring may acquire quality PPG signals for different rotational orientations on the finger, as finger properties such as skin tone, thickness, and blood circulation may vary in different portions of the finger. Additionally, the availability of different transmitter wavelengths may provide options for acquiring PPG signals in different scenarios (e.g., during user movement or sleep).

For example, a wearable device may activate a first combination of optical sensors. The first combination of optical sensors may include a set of transmitter sensors from a plurality of transmitter sensors and a set of receiver sensors from a plurality of receiver sensors of the wearable electronic device. In some cases, the plurality of transmitter sensors may include at least one transmitter sensor of a first wavelength, at least one transmitter sensor of a second wavelength, and at least one transmitter sensor of a third wavelength. In some implementations, at least one optical sensor of the first combination of optical sensors may be positioned under a protrusion on an inner surface of the wearable electronic device. The wearable device may measure, at the set of receiver sensors at a first time, one or more signals from the set of transmitter sensors, and determine a signal quality metric associated with the one or more signals. The wearable device may select a second combination of optical sensors for use at a second time based on the signal quality metric.

Aspects of the disclosure are initially described in the context of systems supporting physiological data collection from users via wearable devices. Aspects are then described with reference to examples of wearable electronic devices, and a process flow. Aspects of the disclosure are further illustrated by and described with reference to apparatus diagrams, system diagrams, and flowcharts that relate to a configurable PPG system.

FIG. 1 illustrates an example of a system 100 that supports a configurable PPG system in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch or wrist-worn wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, that may measure physiological parameters and process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that may emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, respiration data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time when a user 102 is asleep, and classify periods of time when the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time when the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for selecting optical sensors from a set of optical sensors on a wearable electronic device. In particular, the system 100 illustrated in FIG. 1 may support techniques that allow a wearable device to change a set of sensors being used to measure data associated with a user 102-a. The wearable device may change the set of sensors based on one or more metrics, such as signal quality, signal strength, temperature, motion, time of day, etc.

For example, a wearable device, such a ring 104-a, may activate a first combination of optical sensors. The first combination of optical sensors may include a set of transmitter sensors from a plurality of transmitter sensors and a set of receiver sensors from a plurality of receiver sensors of the wearable electronic device. In some cases, the plurality of transmitter sensors may include at least one transmitter sensor of a first wavelength, at least one transmitter sensor of a second wavelength, and at least one transmitter sensor of a third wavelength. In some implementations, at least one optical sensor of the first combination of optical sensors may be positioned under a protrusion on an inner surface of the wearable electronic device. The wearable device may measure, at the set of receiver sensors at a first time, one or more signals from the set of transmitter sensors, and determine a signal quality metric associated with the one or more signals. The wearable device may select a second combination of optical sensors for use at a second time based on the signal quality metric.

In some cases, the ring 104-a may determine heart rate data based on the PPG monitoring. Optical sensor selection and PPG monitoring may be performed by any of the components of the system 100, including the ring 104-a, the user device 106-a associated with User 1, the one or more servers 110, or any combination thereof. Upon determination of heart rate data, the system 100 may selectively cause the GUI of the user device 106-a to display all or a subset of the heart rate data.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
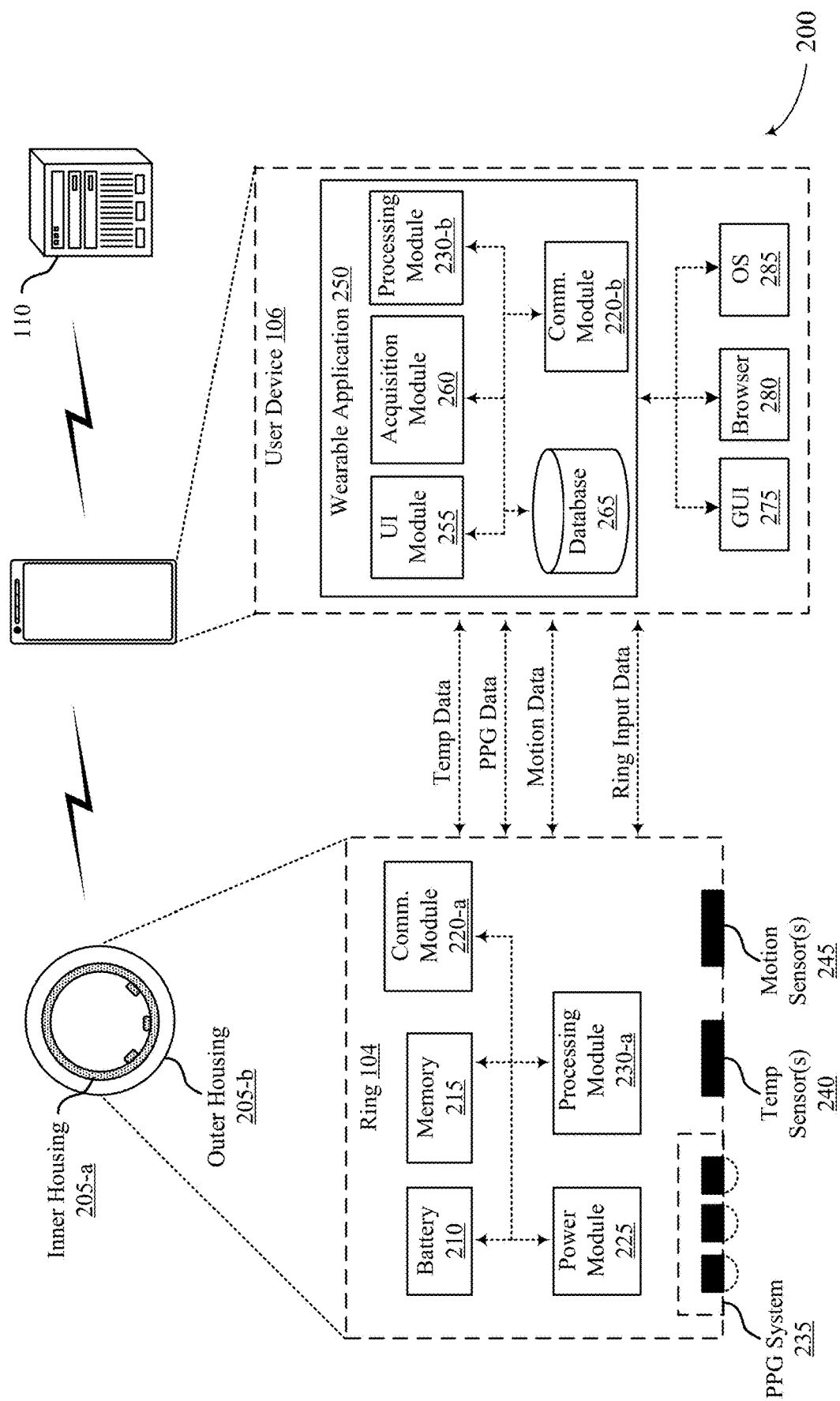

FIG. 2 illustrates an example of a system 200 that supports a configurable PPG system in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium that may provide strength and abrasion resistance at a relatively light weight. The outer housing 205-b may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, and in such case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate may be stored in memory 215 and may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, blood oxygen saturation, and other circulatory parameters.

In some implementations, the PPG system 235 may be configured as a reflective PPG system 235 that the optical receiver(s) receive transmitted light that is reflected through the region of the user's finger. In some implementations, the PPG system 235 may be configured as a transmissive PPG system 235 and the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS) 285, a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be preprocessed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time when the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5°° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for selecting optical sensors from a set of optical sensors of a wearable electronic device. The wearable device may change (e.g., dynamically switch) the set of sensors based on one or more metrics, such as signal quality, signal strength, temperature, motion, time of day, etc. Additionally or alternatively, the system 200 may adjust other parameters associated with the activation of the optical transmitters, the activation of the optical receivers, or both. For example, the system 200 may adjust a sampling rate of one or more of the optical receivers based on signal quality or the like that may enhance battery life when the measured signal quality is relatively good. In some examples, the system 200 may adjust a power of the optical transmitters (e.g., adjust an LED burn time or burn power), based on a signal quality or similar quality metric. In such examples, the system 200 may dynamically adjust one or more measurement parameters (e.g., a combination of sensors to activate, sampling rate, power output, etc.) to optimize for measurement accuracy, battery life, or some other parameter. In some aspects, the ring 104, user device 106, the servers 110 of the system 200 or any combination of these components may be configured to perform such selecting and adjusting.

For example, a wearable device, such as a ring 104, may activate a first combination of optical sensors, such as optical sensors associated with the PPG system 235. The first combination of optical sensors may include a set of transmitter sensors (e.g., LEDs) from a plurality of transmitter sensors and a set of receiver sensors (e.g., photodetectors) from a plurality of receiver sensors of the wearable electronic device. In some cases, the plurality of transmitter sensors may include at least one transmitter sensor of a first wavelength, at least one transmitter sensor of a second wavelength, and at least one transmitter sensor of a third wavelength. In some implementations, at least one optical sensor of the first combination of optical sensors may be positioned under a protrusion (e.g., a dome or raised surface) on an inner surface of the wearable electronic device. The wearable device may measure, at the set of receiver sensors at a first time, one or more signals from the set of transmitter sensors, and determine a signal quality metric associated with the one or more signals. The wearable device may select a second combination of optical sensors for use at a second time based on the signal quality metric. Additionally or alternatively, the wearable device may adjust one or more measurement parameters based on the signal quality metric.

In some cases, the ring 104 may determine heart rate data based on the PPG monitoring. Optical sensor selection and PPG monitoring may be performed by any of the components of the system 200, including the ring 104, the user device 106, the one or more servers 110, or any combination thereof.

Figure 3:
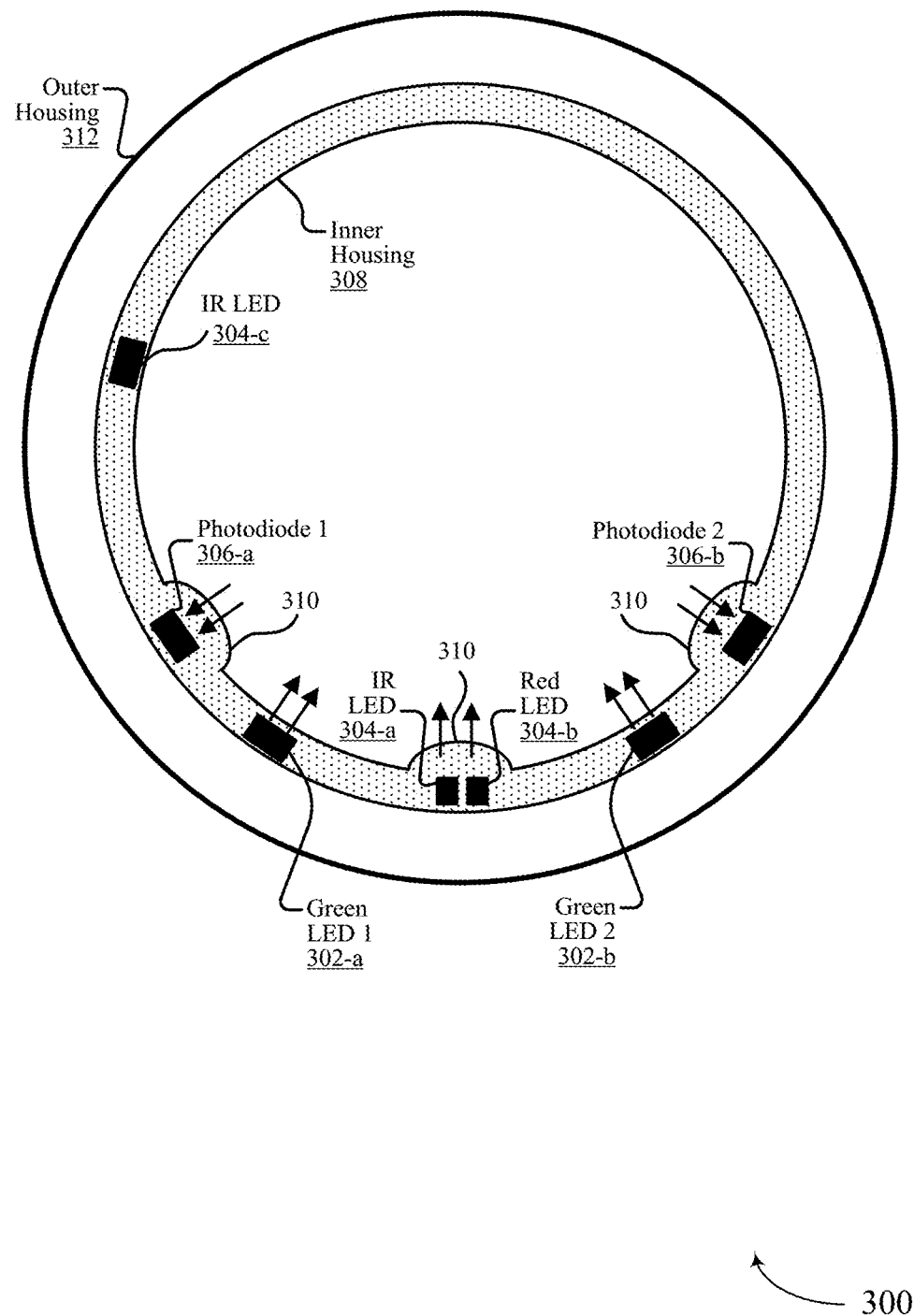
FIGS. 3 through 9 illustrate examples of wearable electronic devices that support a configurable PPG system in accordance with aspects of the present disclosure.

FIG. 3 illustrates an example of a wearable electronic device 300 that supports a configurable PPG system in accordance with aspects of the present disclosure. The wearable electronic device 300 may implement, or be implemented by, the system 100, or the system 200, or both. In particular, the wearable electronic device 300 illustrates an example of a ring 104 (e.g., wearable device 104), as described with reference to FIGS. 1 and 2. The wearable electronic device 300 may include one or more green LEDs 302 in different locations of the wearable electronic device 300. In FIG. 3, the wearable electronic device 300 may include two green LEDs 302 (e.g., LED 302-a, LED 302-b) that are located between IR LED 304-a and red LEDs 304-b and photodiodes 306-a, 306-b (e.g., photodetectors, optical receivers, etc.). In some implementations, a first green LED 302-a (Green LED 1) may be located between a first photodiode 306-a (photodiode 1) and the IR/red LEDs 304-a, 304-b. In some implementations, a second green LED 302-b (Green LED 2) may be located between a second photodiode 306-b (photodiode 2) and the IR/red LEDs 304-b.

In FIG. 3, the two green LEDs 302-a, 302-b are located under a circular portion of an inner housing 308 of the wearable electronic device 300 between protrusions of the circular portion of the inner housing 308 of the wearable electronic device 300. The wearable electronic device 300 may also include an outer housing 312. The location and layout of the LEDs and photodetectors may be arranged to improve certain measurements. For example, the green LED 302-b (Green LED 2) and the photodiode 306-b (photodiode 2) may be positioned and angled such that light emitted from the green LED 302-b (Green LED 2) may be easily captured by the photodiode 306-b (photodiode 2) after reflecting from a finger of a user wearing the wearable electronic device 300. Similarly, light emitted from the green LED 302-a (Green LED 1) may be captured by the photodiode 306-a (photodiode 1). As described herein, the wearable electronic device 300 may select between different combinations of LEDs and photodetectors based on a signal quality metric. For example, the wearable electronic device 300 may select a combination including the green LED 302-a (Green LED 1) and the photodiode 306-a (photodiode 1) for measurements at a first time, but may then switch to a combination including the green LED 302-b (Green LED 2) and the photodiode 306-b (photodiode 2) at a second time based on a signal quality metric (e.g., a measured signal quality).

In FIGS. 3 through 7, photodiodes may sample adjacent green LEDs 302 (e.g., one or more nearest green LEDs). For example, in FIG. 3, the photodiode 306-a (photodiode 1) may generate a PPG signal in response to light received from the green LED 302-a (Green LED 1). In another example, in FIG. 3, the photodiode 306-b (photodiode 2) may generate a PPG signal in response to light received from the green LED 302-b (Green LED 2). In some cases, the green LEDs 302 may be arranged (e.g., separated) such that a transmission of green light from the green LED 302-a (Green LED 1) to the photodiode 306-b (photodiode 2), or from the green LED 302-b (Green LED 2) to the photodiode 306-a (photodiode 1), is minimized or eliminated. In these arrangements, the photodiodes 306 may be limited to detecting the adjacent green LEDs 302. The inclusion of multiple pairs of green LEDs and adjacent photodiodes, as in FIGS. 3 through 7, may help ensure that the green LEDs may be used for different ring orientations. For example, if the ring is rotated from the default orientation, a green LED and adjacent photodiode may still acquire a signal from the underside of the user's finger.

In some implementations, a wearable electronic device 300 (e.g., a ring 104) may be configured to use a single transmitter and a single receiver to generate PPG signals. The transmitter and receiver combination used to generate the PPG signal may be referred to as a "transmitter-receiver combination" or a "transmitter-receiver pair." Example transmitter-receiver pairs of FIGS. 3 through 7 may include: 1) Green LED 1 and photodiode 1, 2) IR LED and photodiode 1, 3) IR LED and photodiode 2, 4) red LED and photodiode 1, 5) red LED and photodiode 2, and 6) Green LED 2 and photodiode 2.

In some implementations, a wearable electronic device (e.g., the wearable electronic device 300) may include a set of receiver sensors positioned on an inner surface of the wearable electronic device. The inner surface may contact a user of the wearable electronic device when the user is wearing the wearable electronic device, at least one receiver sensor of the set of receiver sensors may be positioned under a protrusion on the inner surface of the wearable electronic device. The protrusion may enhance the transmission of light, the collection of light, or both. The one or more protrusions 310 in FIG. 3 is shown for illustration purposes only, and it should be understood the one or more protrusions 310 may be over an LED, a photodetector, or any combination. The wearable electronic device 300 may include a first set of transmitter sensors positioned adjacent the first set of optical sensors on the inner surface. The first set of transmitter sensors may include one or more transmitter sensors of a first wavelength. In some cases, the wearable electronic device 300 may include a second set of transmitter sensors positioned adjacent the second set of optical sensors on the inner surface. The second set of transmitter sensors may include at least one transmitter sensor of a second wavelength and at least one transmitter sensor of a third wavelength.

The first set of receiver sensors may include at least two photodiodes 306. The first set of transmitter sensors may include at least two green LEDs 302, and the second set of optical sensors may include at least one infrared LED 304 and at least one red LED 304. The at least two photodiodes 306 may include a first photodiode 306-a and a second photodiode 306-b arranged with space between the first photodiode and the second photodiode. The at least two green LEDs may include a first green LED 302-a and a second green LED 302-b arranged in the space between the first photodiode 306-a and the second photodiode 306-b. The first green LED 302-a may be positioned to the right of the first photodiode 306-a and the second green LED 302-b may be positioned to the left of the second photodiode 306-b.

The at least one infrared LED 304-a may be positioned to the right of the first green LED 302-a and the at least one red LED 304-b may be positioned to the left of the second green LED 302-b. The at least one infrared LED 304-a and the at least one red LED 304-b may be positioned next to each other. The wearable electronic device 300 may include an additional infrared LED 304-c positioned to the left of the first photodiode 306-a. The additional infrared LED 304-a may be positioned such that light emitted from the additional infrared LED 304-a is directed towards the second photodiode 306-b. This additional infrared LED 304-c may be used to detect whether the ring is being worn (e.g., by determining whether the IR signal is blocked and not received at photodetector 2). The third set of optical sensors may be positioned under a protrusion on the inner surface of the wearable electronic device, and the protrusion may be directed to the user of the wearable electronic device.

In some examples, a wearable electronic device (e.g., a ring 104) may be configured to detect how tightly the wearable electronic device (e.g., the ring 104) is fitting the wearer based on an amount of ambient light detected by the photodetectors, or accelerometer data, or both. For example, a ring may be configured to detect ambient light with one or more receiver sensors of the plurality of receiver sensors and determine that the detected ambient light exceeds a threshold. The threshold may be configured such that ambient light detected above the threshold indicates that the ring is fitting loosely on the finger. The ring may identify a ring fit metric based on determining that the detected ambient light exceeds the threshold.

In some examples, the ring may be able to detect whether the ring is fitting snuggly based on accelerometry data. This accelerometry data can be used independently or in addition to other ring fit data such as ambient light detection. In some examples, the accelerometry data may indicate that the ring bounces or slides or rotates along the finger by identifying additional artifacts in the accelerometry data. For example, if a user is jogging, the predictable motion of the hands moving may appear in the accelerometry data if the ring is fitting snuggly and moving in sync with the hands. However, if the ring is not fitting snuggly, then the accelerometry data may indicate motion that is more inconsistent or noisy than if the ring were fitting snuggly.

Figure 4:
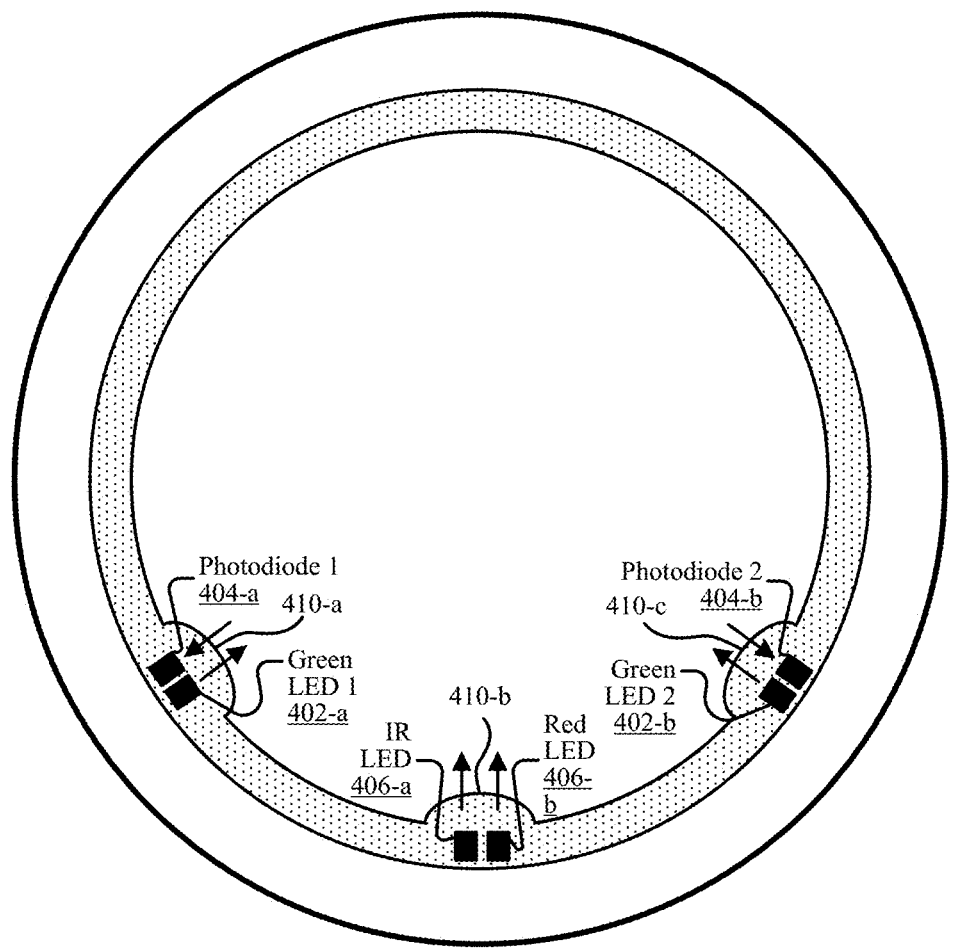

FIG. 4 illustrates an example of a wearable electronic device 400 that supports a configurable PPG system in accordance with aspects of the present disclosure. The wearable electronic device 400 may implement, or be implemented by, the system 100, or the system 200, or both. In particular, the wearable electronic device 400 illustrates an example of a ring 104 (e.g., a wearable device 104), as described with reference to FIGS. 1 and 2. The wearable electronic device 400 may be an example of the wearable electronic device 300 as described with reference to FIG. 3. The wearable electronic device 400 may include one or more green LEDs 402 (e.g., LEDs 402-a, 402-b) in different locations. The green LEDs 402 may be included under protrusions 410 (e.g., protrusions 410-a, 410-b, 410-c) and are collocated with the photodiodes 404 (e.g., photodiodes 404-a, 404-b). Although the green LEDs 402 are located between the photodiodes 404 and the IR/red LEDs 406 under the protrusions 410 in FIG. 4, the green LEDs 402 may be located under the protrusions 410, such that the photodiodes 404 are between the green LEDs 402 and the IR/red LEDs 406.

In FIGS. 3 through 7, photodiodes may sample adjacent green LEDs (e.g., nearest green LEDs). For example, photodiode 1 may generate a PPG signal in response to light received from Green LED 1. In another example, photodiode 2 may generate a PPG signal in response to light received from Green LED 2. In some implementations, in the example of FIG. 4, the photodiodes 404 may generate PPG signals in response to reflected light from the green LEDs 402 under the same protrusion 410.

Figure 5:
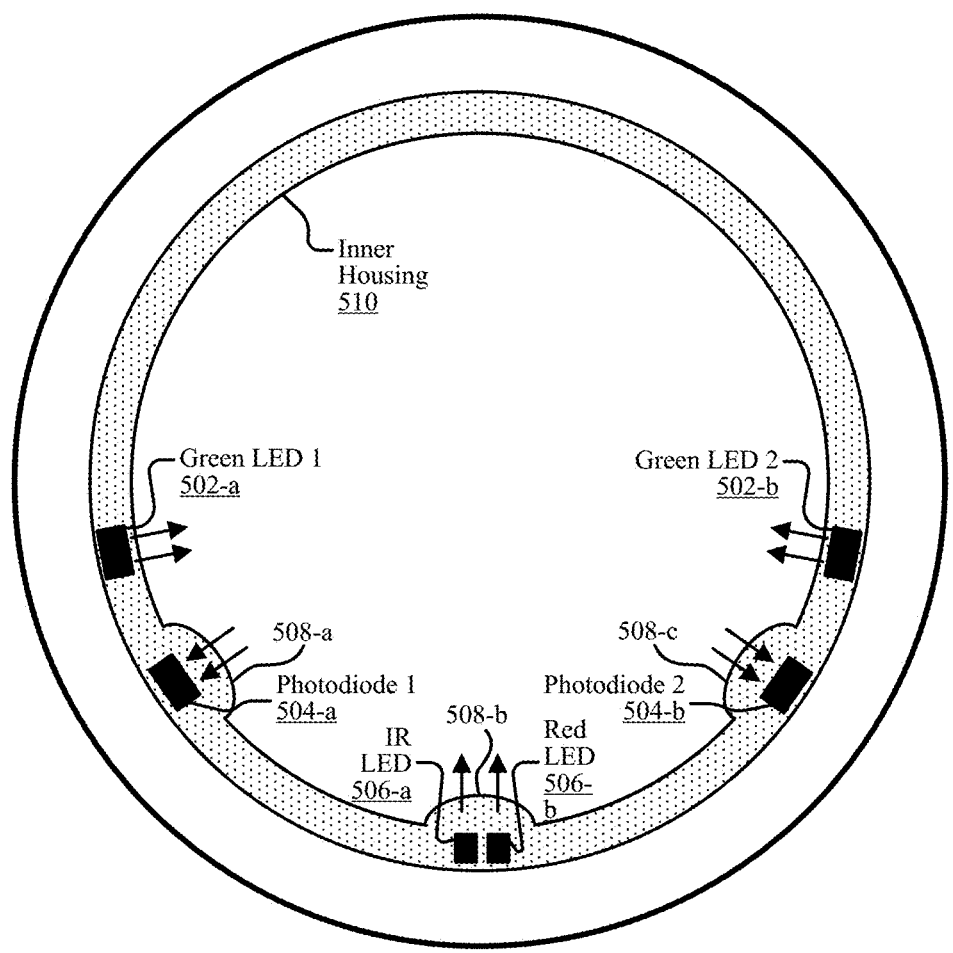

FIG. 5 illustrates an example of a wearable electronic device 500 that supports a configurable PPG system in accordance with aspects of the present disclosure. The wearable electronic device 500 may implement, or be implemented by, the system 100, or the system 200, or both. The wearable electronic device 500 may illustrate an example of a ring 104 (e.g., a wearable device 104), as described with reference to FIGS. 1 and 2. The wearable electronic device 500 may be an example of the wearable electronic devices 300 and the 400 as described with reference to FIGS. 3 and 4. The wearable electronic device 500 may include green LEDs 502 (e.g., green LEDs 502-a, 502-b) in different locations. In the example of FIG. 5, the wearable electronic device 500 illustrates an example ring where the green LEDs 502 are located outside of the protrusions 508-a, 508-b, 508-c (e.g., under a circular inner housing 510) and photodiodes 504-a, 504-b such that the photodiodes 504 and protrusions 508 are located between the green LEDs 502 and the IR/red LEDs 506.

Figure 6:
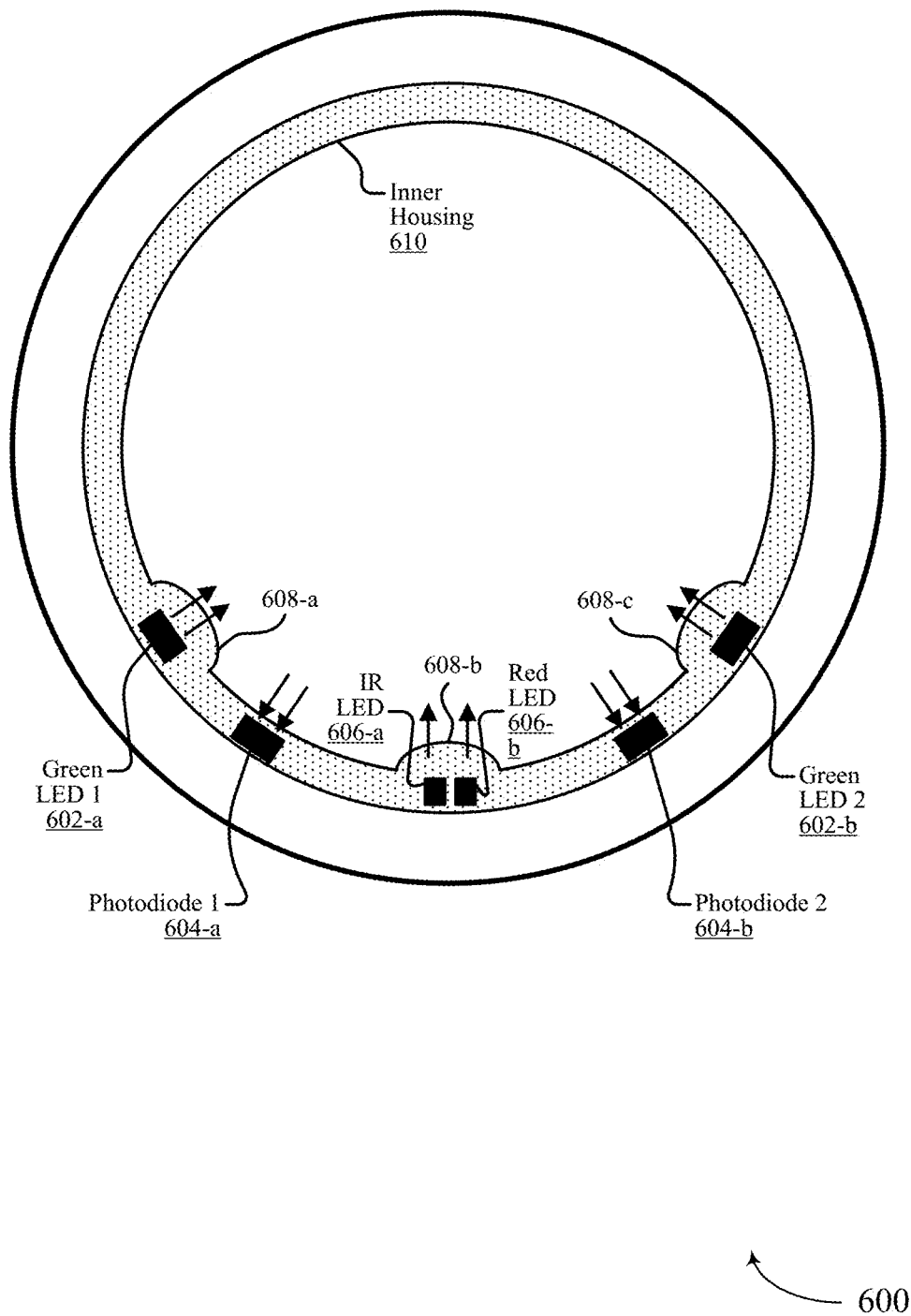

FIG. 6 illustrates an example of a wearable electronic device 600 that supports a configurable PPG system in accordance with aspects of the present disclosure. The wearable electronic device 600 may implement, or be implemented by, the system 100, or the system 200, or both. The wearable electronic device 600 may illustrate an example of a ring 104 (e.g., a wearable device 104), as described with reference to FIGS. 1 and 2. The wearable electronic device 600 may be an example of the wearable electronic devices 300 through 500 as described with reference to FIGS. 3 through 5.

The wearable electronic device 600 may include green LEDs 602 (e.g., green LEDs 602-a, 602-b) in different locations. In the example of FIG. 6, the wearable electronic device 600 illustrates an example ring where the green LEDs 602-a, 602-b are included under protrusions 608-a, 608-c, and the photodiodes 604-a, 604-b are located under a circular inner housing 610 between the green LEDs 602 and the IR/red LEDs 606-a, 606-b. In an alternative non-illustrated ring, the green LEDs 602-a, 602-b may be located under the protrusions 608-a, 608-c and the photodiodes 604-a, 604-b may be located under the circular inner housing 610 and outside of the green LEDs 602 such that the green LEDs 602 are between the photodiodes 604 and the IR/red LEDs 606.

Figure 7:
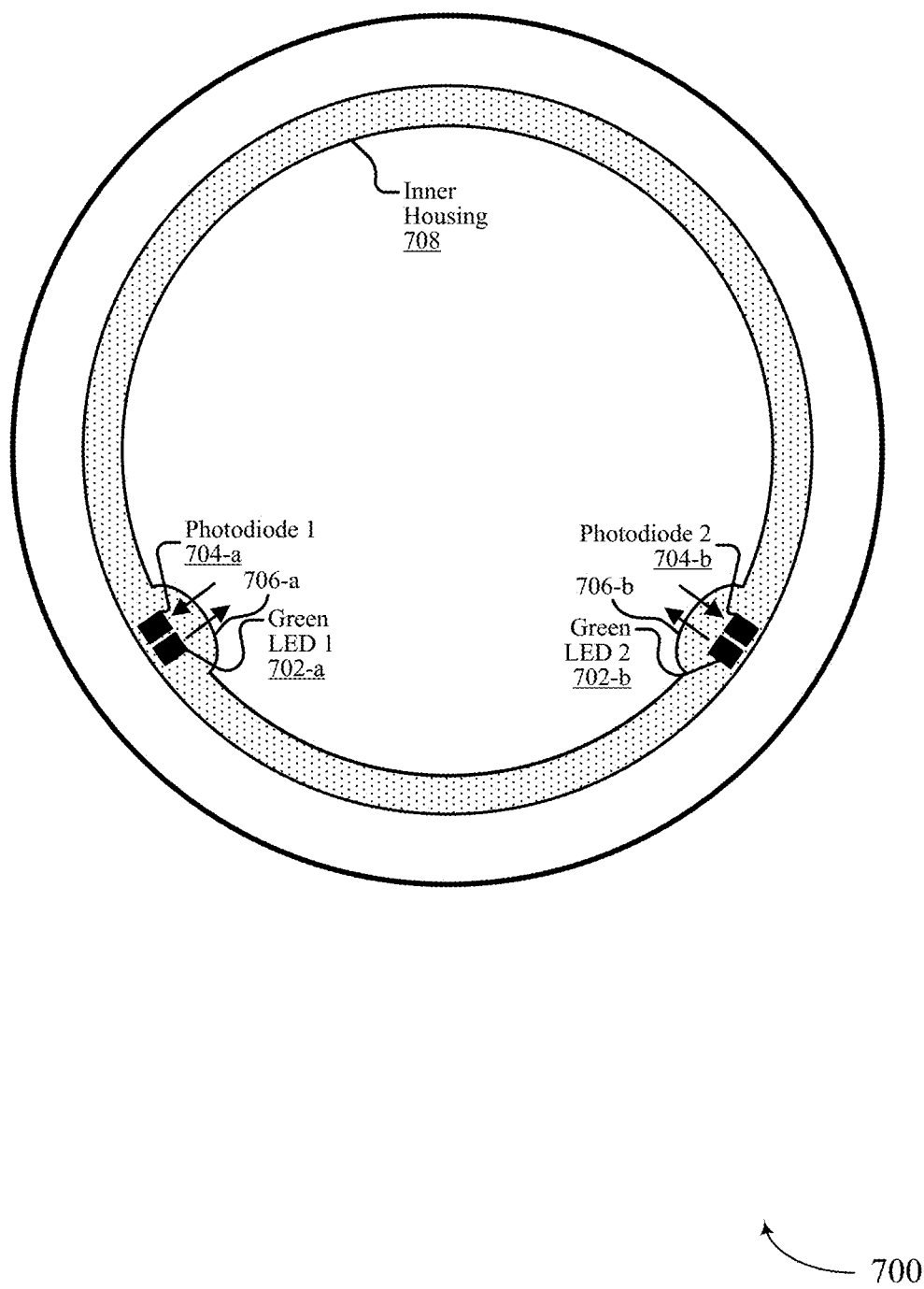

FIG. 7 illustrates an example of a wearable electronic device 700 that supports a configurable PPG system in accordance with aspects of the present disclosure. The wearable electronic device 700 may implement, or be implemented by, the system 100, or the system 200, or both. The wearable electronic device 700 may illustrate an example of a ring 104 (e.g., a wearable device 104), as described with reference to FIGS. 1 and 2. The wearable electronic device 700 may be an example of the wearable electronic devices 300 through 600 as described with reference to FIGS. 3 through 6. In the example of FIG. 7, the wearable electronic device 700 may include green LEDs 702-a, 702-b in different locations. For example, the green LEDs 702-a, 702-b may be located under protrusions 706-a, 706-b in the wearable electronic device 700 and the photodiodes 704-a, 704-b may be located under a circular inner housing 708 between the green LEDs 702.

Figure 8:
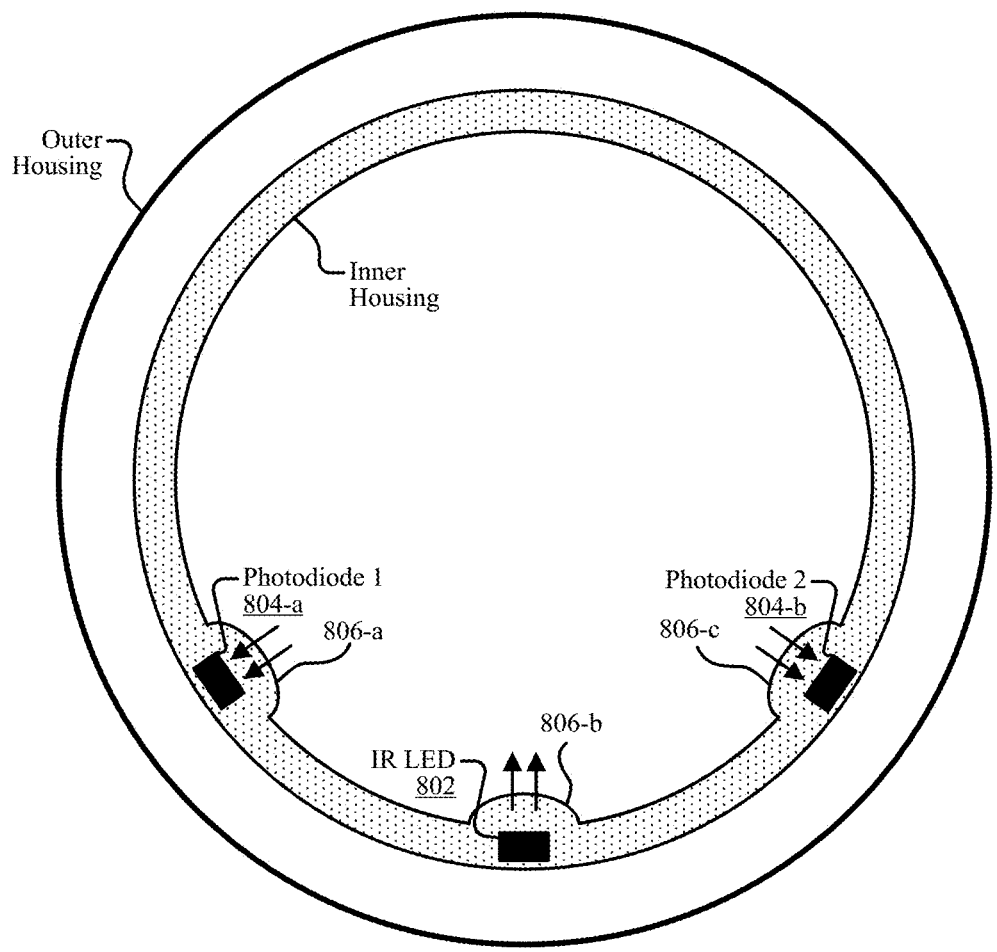

FIG. 8 illustrates an example of a wearable electronic device 800 that supports a configurable PPG system in accordance with aspects of the present disclosure. The wearable electronic device 800 may implement, or be implemented by, the system 100, or the system 200, or both. The wearable electronic device 800 may illustrate an example of a ring 104 (e.g., a wearable device 104), as described with reference to FIGS. 1 and 2. The wearable electronic device 800 may be an example of the wearable electronic devices 300 through 700 as described with reference to FIGS. 3 through 7.

In the example of FIG. 8, the wearable electronic device 800 (e.g., a ring 104) may include a single IR LED 802 that is centrally located at a bottom of the wearable electronic device 800 between two photodiodes 804-a, 804-b. The IR LED 802 may be included under a center protrusion 806-b. The photodiodes 804 may be included under additional protrusions 806-a, 806-c that are equally spaced from the IR LED 802. In this implementation, either photodiode 804 may be used to acquire IR light. For example, the wearable electronic device 800 (e.g., the ring 104) may select at least one of the photodiode 804-a or the photodiode 804-b that generates the best signal of the two photodiodes 804.

A centrally located transmitter between two receivers may help ensure that a quality PPG signal may be obtained from at least one of the two receivers when the wearable electronic device 800 (e.g., the ring 104) is rotated from the default orientation. For example, if the wearable electronic device 800 (e.g., the ring 104) is rotated from the default orientation, one of the receivers may still be located under the user's finger to receive light transmitted into the underside of the finger.

Figure 9:
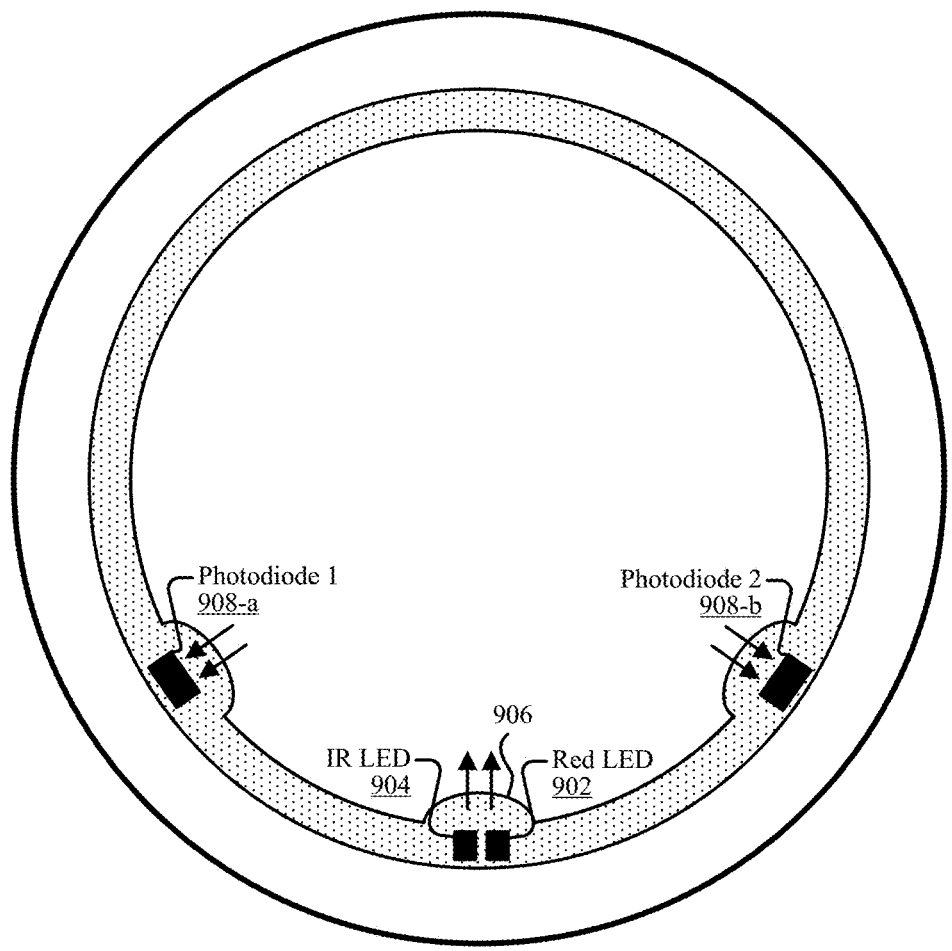

FIG. 9 illustrates an example of a wearable electronic device 900 that supports a configurable PPG system in accordance with aspects of the present disclosure. The wearable electronic device 900 may implement, or be implemented by, the system 100, or the system 200, or both. The wearable electronic device 900 may illustrate an example of a ring 104 (e.g., a wearable device 104), as described with reference to FIGS. 1 and 2. The wearable electronic device 900 may be an example of the wearable electronic devices 300 through 800 as described with reference to FIGS. 3 through 8.

The wearable electronic device 900 may include transmitter and receivers from FIG. 8. In the example of FIG. 8, the wearable electronic device 900 (e.g., a ring 104) may include a red LED 902 that is located along with an IR LED 904 (e.g., next to the IR LED 904). For example, the red LED 902 and IR LED 904 may be collocated under a center protrusion 906 between two photodiodes 908-a, 908-b (e.g., photodiode 1 and photodiode 2). In this example, the red LED 902 may transmit light through similar paths as the IR LED 904. The wearable electronic device 900 (e.g., the ring 104) may use the red LED 902 to perform oxygen saturation measurements (e.g., SpO2). Collocating the red LED 902 and the IR LED 904 under the same protrusion 906 may cause the red LED 902 and the IR LED 904 to transmit, into a finger of a user wearing the wearable electronic device 900 (e.g., the ring 104), in a similar manner (e.g., in similar physical locations on the finger) that may cause the LED signals to be affected similarly during transmission. As described herein, reflections may be minimized when transmitted into the interface between the center protrusion and the skin.

Figure 10:
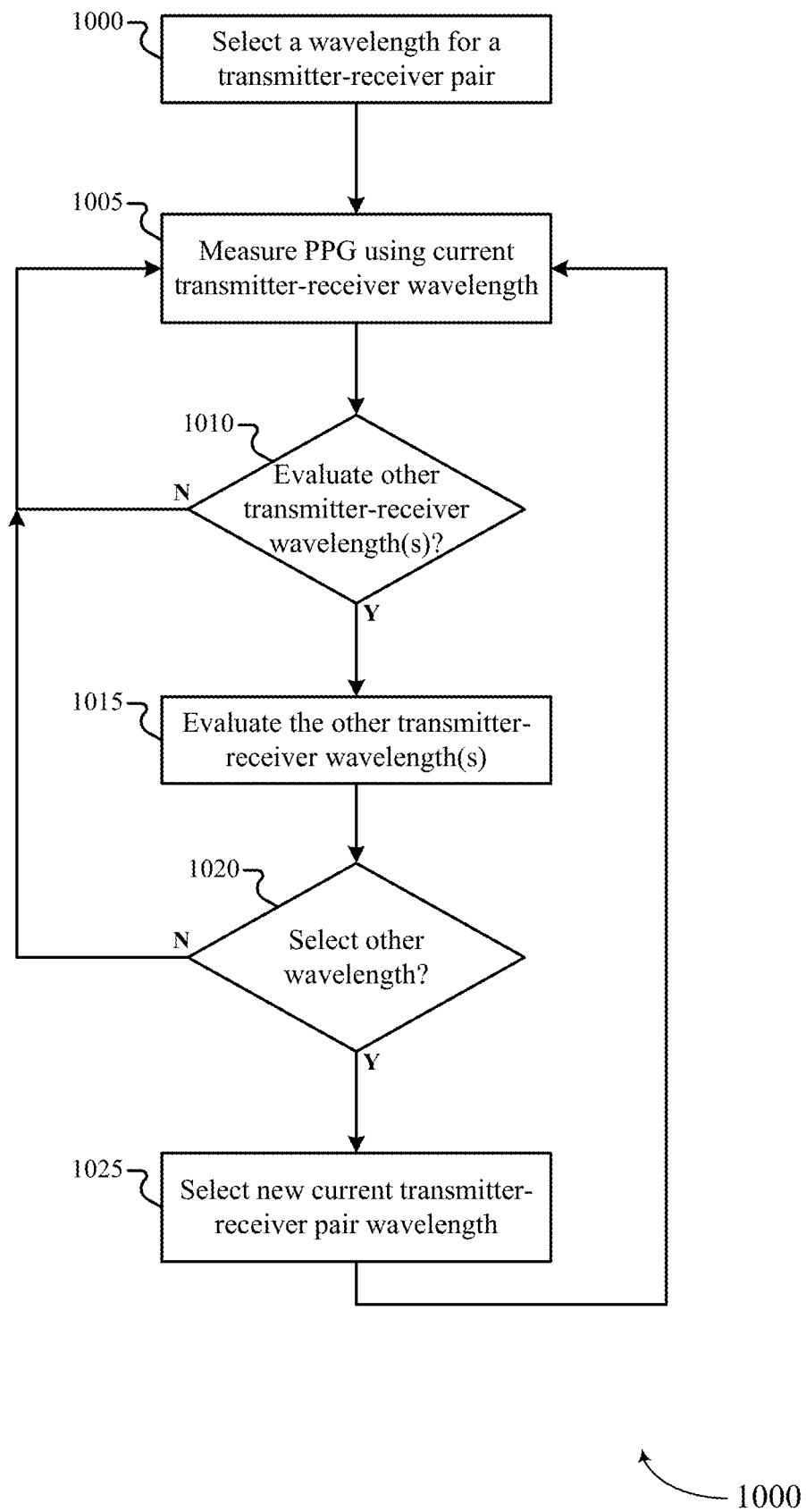
FIG. 10 illustrates an example of a process flow that supports a configurable PPG system in accordance with aspects of the present disclosure.

FIG. 10 illustrates an example of a process flow 1000 that supports a configurable PPG system in accordance with aspects of the present disclosure. The operations of the process flow 1000 may be implemented by a wearable device or its components as described herein. For example, the operations of the process flow 1000 may be performed by a wearable device as described with reference to FIGS. 1 through 9. In some examples, a wearable device may execute a set of instructions to control the functional elements of the wearable device to perform the described functions. Additionally or alternatively, the wearable device may perform aspects of the described functions using special-purpose hardware.

At 1000, the wearable device may select a wavelength for a transmitter-receiver pair of the wearable device. In some implementations, the wearable device may activate or control a transmitter-receiver pair having a first wavelength in order to measure PPG signals. For example, the wearable device may initially activate/control an IR transmitter and photodiode or a green transmitter-photodiode pair. At 1005, the wearable device may measure a PPG using a current transmitter-receiver wavelength. For example, the wearable device may acquire a PPG signal using the selected transmitter-receiver pair of the first wavelength over time until the processing module determines that another wavelength of transmitter should be evaluated.

At 1010, the wearable device may evaluate other transmitter-receiver wavelength(s). In some implementations, the wearable device may determine whether another wavelength of a transmitter should be evaluated. For example, the wearable device may determine whether another wavelength of transmitter should be evaluated based on selection criteria, such as wavelength selection criteria, transmitter selection criteria, and/or receiver selection criteria described herein. The wavelength selection criteria may include, but are not limited to, time of day/night, an amount of user movement, and temperature, as described herein.

The selection criteria evaluated by the wearable device to determine whether to evaluate other wavelengths may depend on the currently selected wavelength and/or the next possible selected wavelength. For example, the wearable device may be configured to evaluate other wavelengths when a transition to the other wavelengths may be beneficial (e.g., based on current conditions). In some examples, the wearable device may be configured to evaluate a green wavelength when the ring is currently using an IR wavelength if motion/exercise is detected, assuming a green transmitter-receiver pair may be more effective during motion. In some other examples, the wearable device may be configured to evaluate a green wavelength when the ring is currently using an IR wavelength if it is during the daytime, assuming that a green transmitter-receiver pair may be less distracting during the day. If the wearable device is currently using a green transmitter-receiver pair, the wearable device may be configured to evaluate an IR wavelength when motion/exercise ends and/or during nighttime. In other examples, the wearable device may be configured to evaluate an IR wavelength when the wearable device is currently using a green wavelength if temperature (e.g., a user/ambient temperature) is relatively low, assuming that an IR transmitter-receiver pair is more effective in colder temperatures. For either current wavelength, the wearable device may be configured to evaluate other wavelengths in the case that signal strength is less than sufficient using transmitters of the current wavelength.

In some implementations, the criteria for transitioning between PPG wavelengths (e.g., IR or green) may differ, depending on the current wavelength and the specific wavelength transition to be made. For example, since green LEDs may be preferable during user activity, movement criteria may tend to favor selection of green LEDs by requiring less movement for a transition from IR to green (e.g., relative to a lack of movement for a green to IR transition). If the wearable device determines that a new transmitter wavelength should not be evaluated, at 1010, the wearable device may generate the PPG signal using the first wavelength. Note that the wearable device may switch transmitters and/or receivers within the same wavelength at 1005 in order to acquire a better signal (e.g., according to FIGS. 6 and -7). If the wearable device determines that a new transmitter wavelength should be evaluated, at 1010, the wearable device may evaluate the other transmitter-receiver wavelength(s) (e.g., the second wavelength) at 1015. For example, the wearable device may try different transmitter-receiver combinations for the second wavelength at 1015 to determine whether a better signal can be acquired using the second wavelength relative to the first wavelength.

At 1020, the wearable device may determine whether to select the other wavelength(s) (e.g., the second wavelength over the first wavelength). The wearable device may perform the determination based on any selection criteria described herein, such as time of day, user movement, temperature, and signal quality. If the wearable device does not select the second wavelength, the process flow 1000 continues at 1005 where the PPG signal is generated using the first wavelength. If the wearable device selects the second wavelength at 1020, the process flow continues at 1025 where the wearable device selects a new transmitter-receiver pair wavelength. The process flow then continues at 1005, where the wearable device measures the PPG signal according to the new current transmitter-receiver pair wavelength. The wearable device may then continue measuring PPG signals, evaluating other wavelengths, and changing transmitter wavelengths according to operations performed at 1005 through 1025.

Although the wearable device may acquire data (e.g., PPG data, temperature data, and motion data) and perform determinations based on the acquired data locally on the wearable device, in some implementations, the wearable device may transmit data to another computing device (e.g., a user device) for processing. In these implementations, the computing device (e.g., the user device) may process the acquired data and send commands/data back to the wearable device. The wearable device may then perform operations based on the received data/commands. In some examples, the computing device may determine when to switch wavelengths, transmitters, and/or receivers as described herein. The computing device may then send data/commands to the wearable device that may cause the wearable device to switch wavelengths, transmitters, and/or receivers. Accordingly, the data acquisition, processing, determinations, and commands described herein may be implemented by the wearable device and/or other computing devices to different extents.

Figure 11:
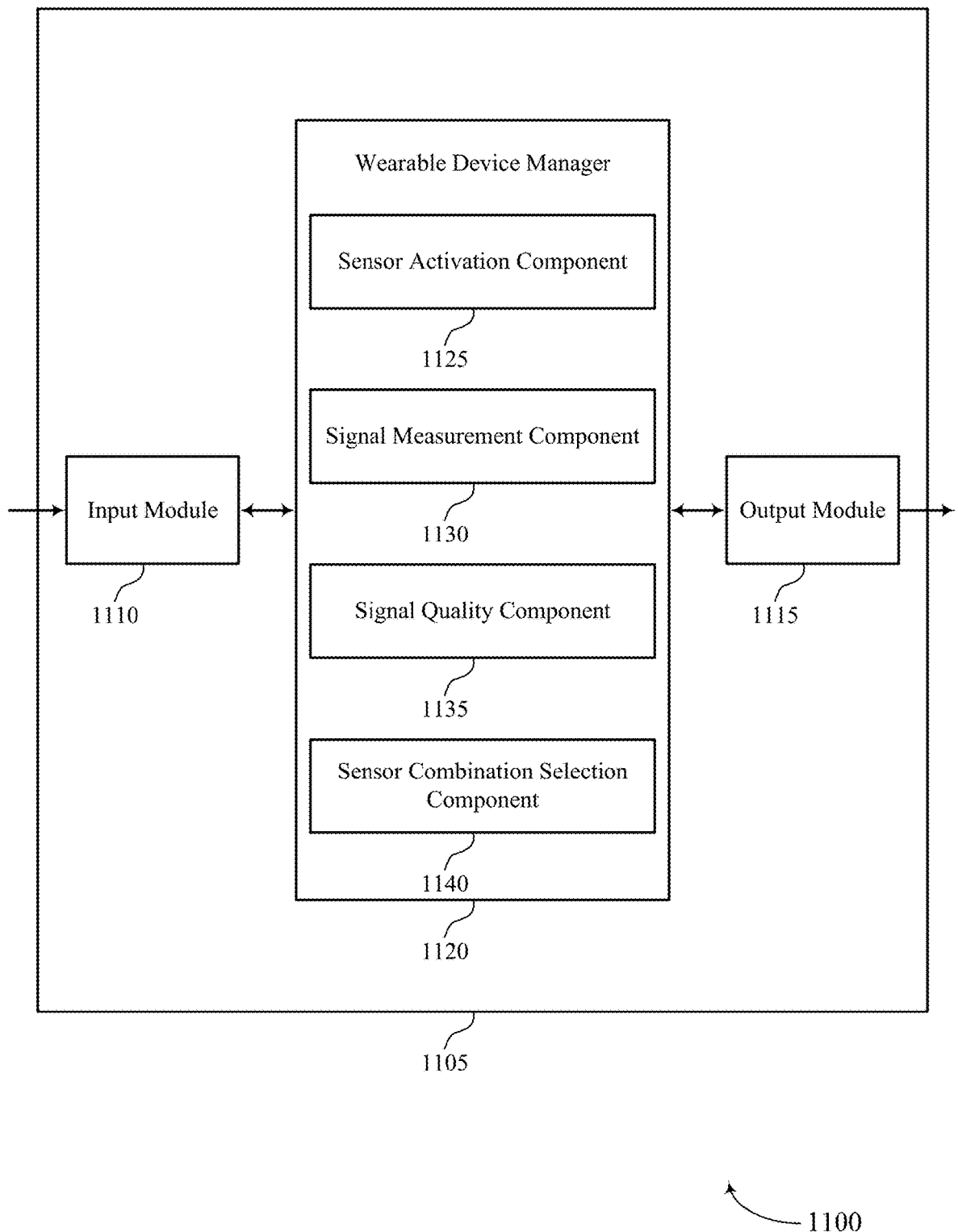
FIG. 11 shows a block diagram of an apparatus that supports a configurable PPG system in accordance with aspects of the present disclosure.

FIG. 11 shows a block diagram 1100 of a device 1105 that supports a configurable PPG system in accordance with aspects of the present disclosure. The device 1105 may include an input module 1110, an output module 1115, and a wearable device manager 1120. The device 1105 may also include a processor. Each of these components may be in communication with one another (e.g., via one or more buses).

For example, the wearable device manager 1120 may include a sensor activation component 1125, a signal measurement component 1130, a signal quality component 1135, a sensor combination selection component 1140, or any combination thereof. In some examples, the wearable device manager 1120, or various components thereof, may be configured to perform various operations (e.g., receiving, monitoring, transmitting) using or otherwise in cooperation with the input module 1110, the output module 1115, or both. For example, the wearable device manager 1120 may receive information from the input module 1110, send information to the output module 1115, or be integrated in combination with the input module 1110, the output module 1115, or both to receive information, transmit information, or perform various other operations as described herein.

The wearable device manager 1120 may support measuring optical signals by a wearable electronic device in accordance with examples as disclosed herein. The sensor activation component 1125 may be configured as or otherwise support a means for activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The signal measurement component 1130 may be configured as or otherwise support a means for measuring, at the set of receiver sensors at a first time, one or more signals from the set of transmitter sensors. The signal quality component 1135 may be configured as or otherwise support a means for determining a signal quality metric associated with the one or more signals. The sensor combination selection component 1140 may be configured as or otherwise support a means for selecting a second combination of optical sensors for use at a second time based at least in part on the signal quality metric.

Figure 12:
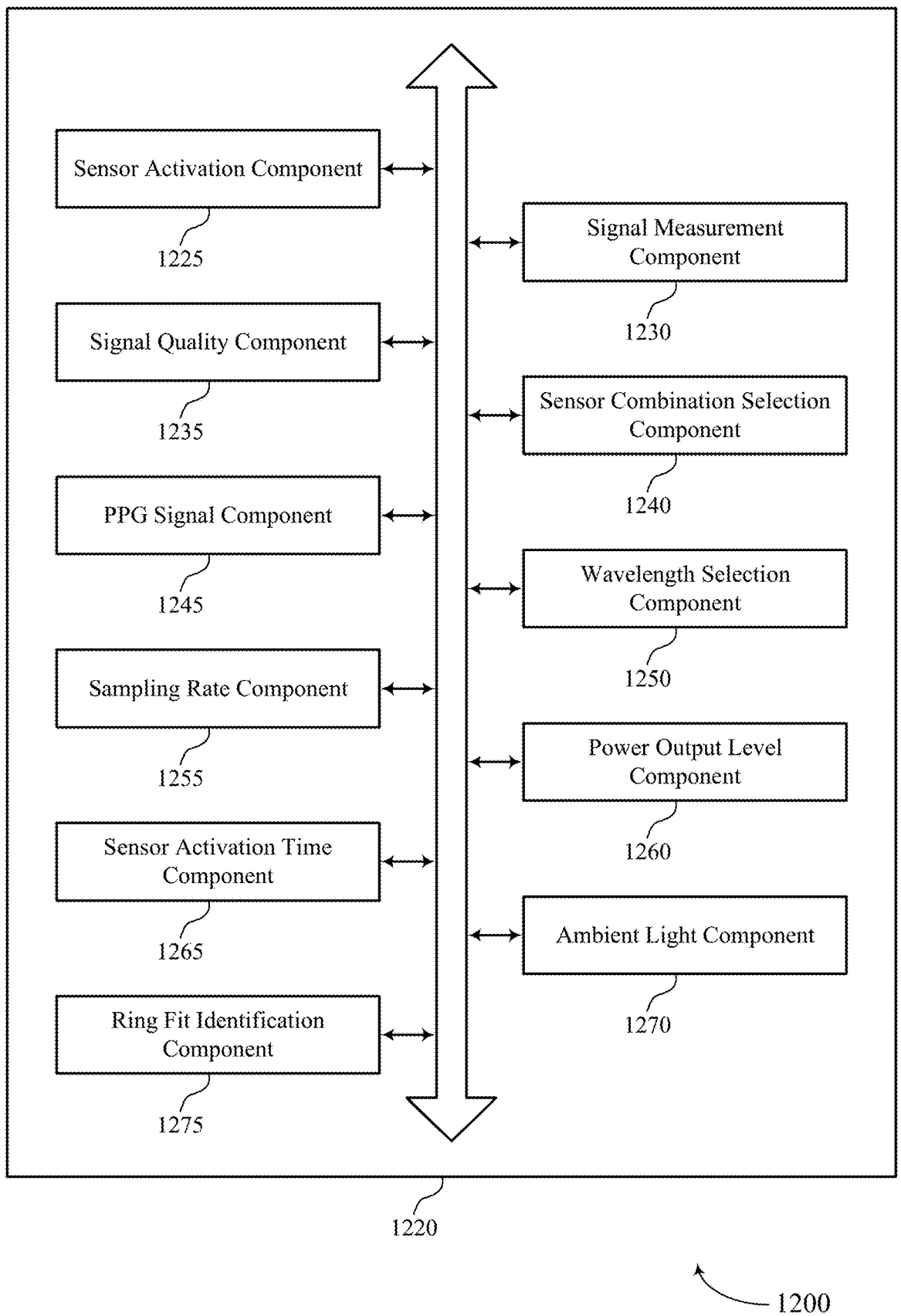
FIG. 12 shows a block diagram of a wearable device manager that supports a configurable PPG system in accordance with aspects of the present disclosure.

FIG. 12 shows a block diagram 1200 of a wearable device manager 1220 that supports a configurable PPG system in accordance with aspects of the present disclosure. The wearable device manager 1220 may be an example of aspects of a wearable device manager or a wearable device manager 1120, or both, as described herein. The wearable device manager 1220, or various components thereof, may be an example of means for performing various aspects of a configurable PPG system as described herein. For example, the wearable device manager 1220 may include a sensor activation component 1225, a signal measurement component 1230, a signal quality component 1235, a sensor combination selection component 1240, a PPG signal component 1245, a wavelength selection component 1250, a sampling rate component 1255, a power output level component 1260, a sensor activation time component 1265, an ambient light component 1270, a ring fit identification component 1275, or any combination thereof. Each of these components may communicate, directly or indirectly, with one another (e.g., via one or more buses).

The wearable device manager 1220 may support measuring optical signals by a wearable electronic device in accordance with examples as disclosed herein. The sensor activation component 1225 may be configured as or otherwise support a means for activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The signal measurement component 1230 may be configured as or otherwise support a means for measuring, at the set of receiver sensors at a first time, one or more signals from the set of transmitter sensors. The signal quality component 1235 may be configured as or otherwise support a means for determining a signal quality metric associated with the one or more signals. The sensor combination selection component 1240 may be configured as or otherwise support a means for selecting a second combination of optical sensors for use at a second time based at least in part on the signal quality metric.

In some examples, to support selecting the second combination of optical sensors, the sensor combination selection component 1240 may be configured as or otherwise support a means for selecting a second set of transmitter sensors, a second set of receiver sensors, or a combination thereof based at least in part on the signal quality metric.

In some examples, the second set of transmitter sensors and the second set of receiver sensors are positioned around the wearable electronic device. In some examples, selecting the second combination of optical sensors is based at least in part on the positioning of the second set of transmitter sensors and the second set of receiver sensors.

In some examples, the wearable electronic device comprises a first photodiode and a second photodiode, the first photodiode and the second photodiode located under a first protrusion and a second protrusion, respectively, in the wearable electronic device.

In some examples, the at least one transmitter sensor of the first wavelength comprises a first green LED and a second green LED, the first green LED positioned to the right of the first photodiode and the second green LED positioned to the left of the second photodiode.

In some examples, the at least one transmitter sensor of the second wavelength comprises an infrared LED, the infrared LED positioned to the right of the first green LED.

In some examples, the at least one transmitter sensor of the third wavelength comprises a red LED, the red LED positioned to the left of the second green LED, the red LED and the infrared LED positioned next to one another.

In some examples, the infrared LED and the red LED are positioned under a third protrusion in the wearable electronic device.

In some examples, to support selecting the second combination of optical sensors, the sensor combination selection component 1240 may be configured as or otherwise support a means for selecting a pair of optical sensors, the pair of optical sensors comprising at least one transmitter optical sensor and at least one receiver optical sensor.

In some examples, to support measuring the one or more signals, the PPG signal component 1245 may be configured as or otherwise support a means for measuring, by the set of receiver sensors, a PPG signal from the set of transmitter sensors.

In some examples, to support determining the signal quality metric, the PPG signal component 1245 may be configured as or otherwise support a means for determining an amplitude of the PPG signal, an amount of noise in the PPG signal, a form of the PPG signal, a power consumption associated with determining the PPG signal, or a combination thereof.

In some examples, the wavelength selection component 1250 may be configured as or otherwise support a means for selecting a wavelength from a set of wavelengths based at least in part on a set of parameters for use in generating the one or more signals, wherein selecting the second combination of optical sensors is based at least in part on the selected wavelength.

In some examples, to support selecting the second combination of optical sensors, the wavelength selection component 1250 may be configured as or otherwise support a means for selecting between the at least one transmitter sensor of the first wavelength or the at least one transmitter sensor of the second wavelength.

In some examples, to support determining the signal quality metric, the signal quality component 1235 may be configured as or otherwise support a means for determining a signal quality, a time of day, a motion of a user of the wearable electronic device, a temperature, a wavelength associated with the first set of optical sensors, or a combination thereof.

In some examples, the sampling rate component 1255 may be configured as or otherwise support a means for updating a sampling rate associated with the first combination of optical sensors, the second combination of optical sensors, or both, based at least in part on the signal quality metric.

In some examples, the power output level component 1260 may be configured as or otherwise support a means for updating a power output level associated with the first combination of optical sensors, the second combination of optical sensors, or both, based at least in part on the signal quality metric.

In some examples, the sensor activation time component 1265 may be configured as or otherwise support a means for updating sensor activation time associated with the first combination of optical sensors, the second combination of optical sensors, or both, based at least in part on the signal quality metric.

In some examples, the ambient light component 1270 may be configured as or otherwise support a means for detecting an ambient light with one or more receiver sensors of the plurality of receiver sensors. In some examples, the ambient light component 1270 may be configured as or otherwise support a means for determining that the detected ambient light exceeds a threshold. In some examples, the ring fit identification component 1275 may be configured as or otherwise support a means for identifying a ring fit metric based at least in part on determining that the detected ambient light exceeds the threshold, wherein the ring fit metric indicates a gap between the inner surface of the wearable electronic device and skin of a user wearing the wearable electronic device.

In some examples, the sensor combination selection component 1240 may be configured as or otherwise support a means for activating the infrared LED that is dedicated for finger wearing detection. In some examples, the ring fit identification component 1275 may be configured as or otherwise support a means for determining whether the wearable electronic device is being worn by a user based at least in part on whether the activated infrared LED that is dedicated for finger wearing detection is detected by one or more of the plurality of receiver sensors.

Figure 13:
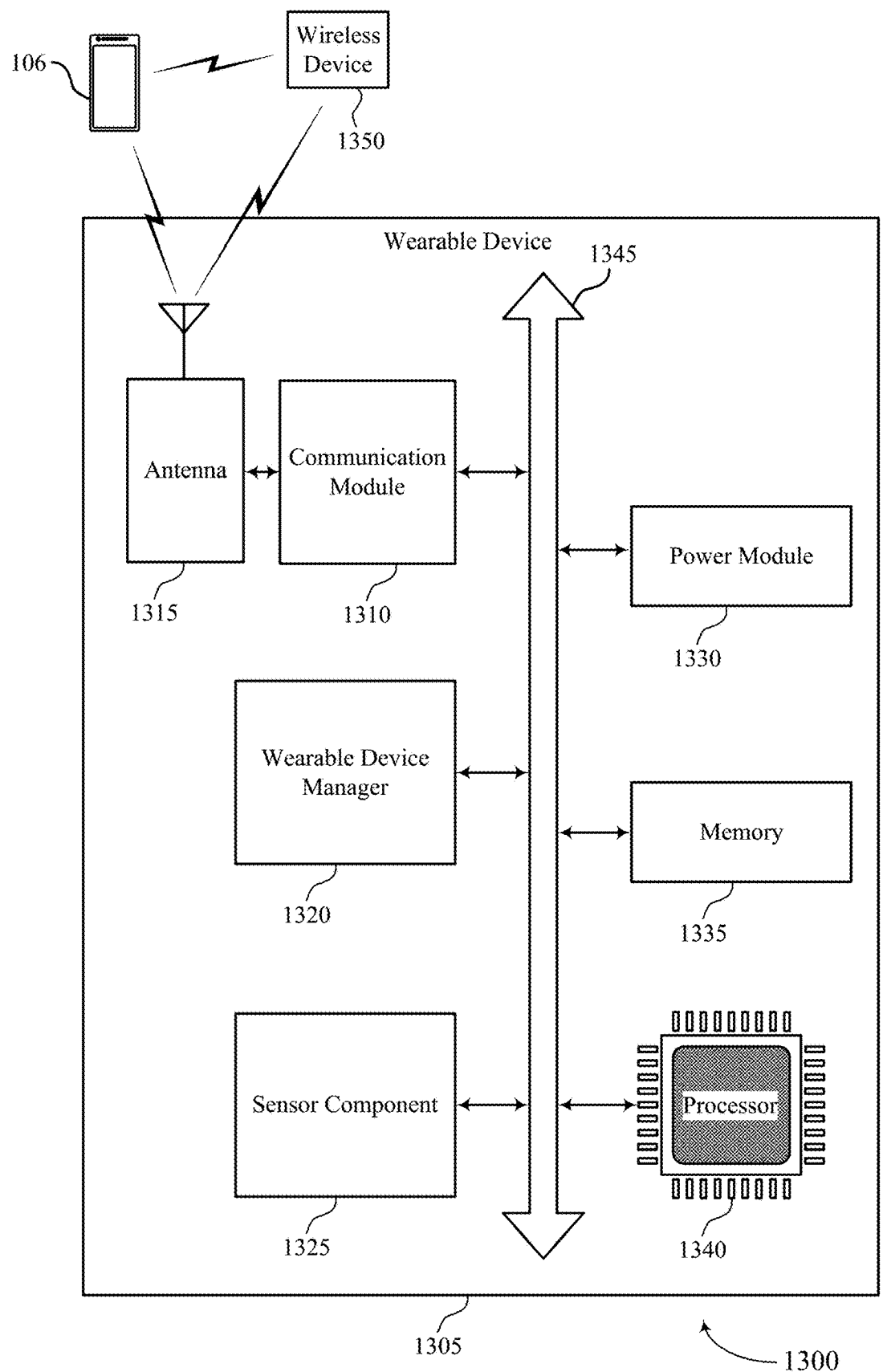
FIG. 13 shows a diagram of a system including a device that supports a configurable PPG system in accordance with aspects of the present disclosure.

FIG. 13 shows a diagram of a system 1300 including a device 1305 that supports a configurable PPG system in accordance with aspects of the present disclosure. The device 1305 may be an example of or include the components of a device 1105 as described herein. The device 1305 may include an example of a wearable device 104, as described previously herein. The device 1305 may include components for bi-directional communications including components for transmitting and receiving communications with a user device 106 and a server 110, such as a wearable device manager 1320, a communication module 1310, an antenna 1315, a sensor component 1325, a power module 1330, a memory 1335, a processor 1340, and a wireless device 1350. These components may be in electronic communication or otherwise coupled (e.g., operatively, communicatively, functionally, electronically, electrically) via one or more buses (e.g., a bus 1345).

The wearable device manager 1320 may support measuring optical signals by a wearable electronic device in accordance with examples as disclosed herein. For example, the wearable device manager 1320 may be configured as or otherwise support a means for activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The wearable device manager 1320 may be configured as or otherwise support a means for measuring, at the set of receiver sensors at a first time, one or more signals from the set of transmitter sensors. The wearable device manager 1320 may be configured as or otherwise support a means for determining a signal quality metric associated with the one or more signals. The wearable device manager 1320 may be configured as or otherwise support a means for selecting a second combination of optical sensors for use at a second time based at least in part on the signal quality metric.

By including or configuring the wearable device manager 1320 in accordance with examples as described herein, the device 1305 may support techniques for measuring PPG signals of a user by supporting dynamic selection of optical sensors for such measurements.

Figure 14:
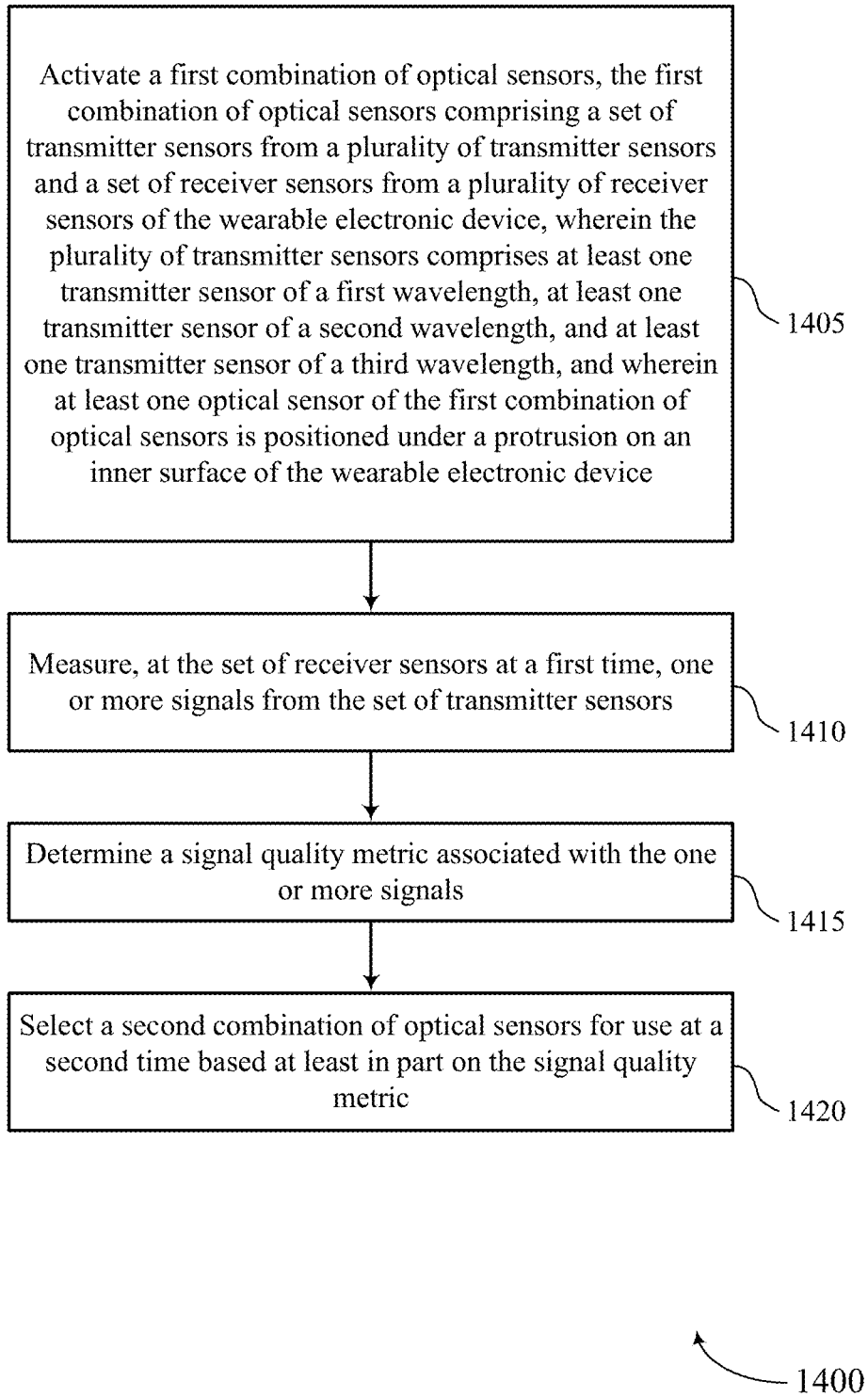
FIGS. 14 through 16 show flowcharts illustrating methods that support a configurable PPG system in accordance with aspects of the present disclosure.

FIG. 14 shows a flowchart illustrating a method 1400 that supports a configurable PPG system in accordance with aspects of the present disclosure. The operations of the method 1400 may be implemented by a wearable device or its components as described herein. For example, the operations of the method 1400 may be performed by a wearable device as described with reference to FIGS. 1 through 13. In some examples, a wearable device may execute a set of instructions to control the functional elements of the wearable device to perform the described functions. Additionally or alternatively, the wearable device may perform aspects of the described functions using special-purpose hardware.

At 1405, the method may include activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The operations of 1405 may be performed in accordance with examples as disclosed herein. In some examples, aspects of the operations of 1405 may be performed by a sensor activation component 1225 as described with reference to FIG. 12.

At 1410, the method may include measuring, at the set of receiver sensors at a first time, one or more signals from the set of transmitter sensors. The operations of 1410 may be performed in accordance with examples as disclosed herein. In some examples, aspects of the operations of 1410 may be performed by a signal measurement component 1230 as described with reference to FIG. 12.

At 1415, the method may include determining a signal quality metric associated with the one or more signals. The operations of 1415 may be performed in accordance with examples as disclosed herein. In some examples, aspects of the operations of 1415 may be performed by a signal quality component 1235 as described with reference to FIG. 12.

At 1420, the method may include selecting a second combination of optical sensors for use at a second time based at least in part on the signal quality metric. The operations of 1420 may be performed in accordance with examples as disclosed herein. In some examples, aspects of the operations of 1420 may be performed by a sensor combination selection component 1240 as described with reference to FIG. 12.

Figure 15:
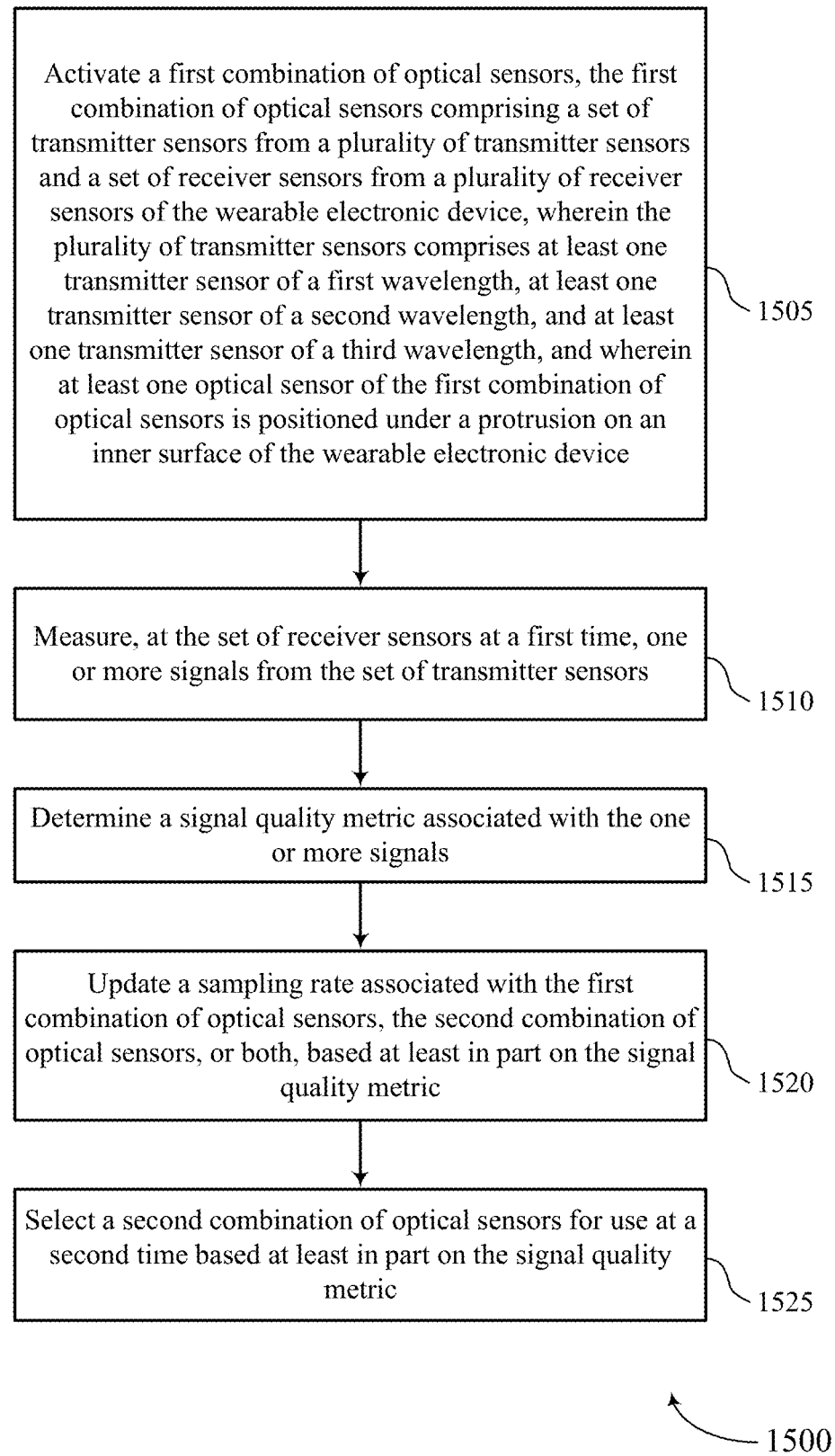

FIG. 15 shows a flowchart illustrating a method 1500 that supports a configurable PPG system in accordance with aspects of the present disclosure. The operations of the method 1500 may be implemented by a wearable device or its components as described herein. For example, the operations of the method 1500 may be performed by a wearable device as described with reference to FIGS. 1 through 13. In some examples, a wearable device may execute a set of instructions to control the functional elements of the wearable device to perform the described functions. Additionally or alternatively, the wearable device may perform aspects of the described functions using special-purpose hardware.

At 1505, the method may include activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The operations of 1505 may be performed in accordance with examples as disclosed herein. In some examples, aspects of the operations of 1505 may be performed by a sensor activation component 1225 as described with reference to FIG. 12.

At 1510, the method may include measuring, at the set of receiver sensors at a first time, one or more signals from the set of transmitter sensors. The operations of 1510 may be performed in accordance with examples as disclosed herein. In some examples, aspects of the operations of 1510 may be performed by a signal measurement component 1230 as described with reference to FIG. 12.

At 1515, the method may include determining a signal quality metric associated with the one or more signals. The operations of 1515 may be performed in accordance with examples as disclosed herein. In some examples, aspects of the operations of 1515 may be performed by a signal quality component 1235 as described with reference to FIG. 12.

At 1520, the method may include updating a sampling rate associated with the first combination of optical sensors, the second combination of optical sensors, or both, based at least in part on the signal quality metric. The operations of 1520 may be performed in accordance with examples as disclosed herein. In some examples, aspects of the operations of 1520 may be performed by a sampling rate component 1255 as described with reference to FIG. 12.

At 1525, the method may include selecting a second combination of optical sensors for use at a second time based at least in part on the signal quality metric. The operations of 1525 may be performed in accordance with examples as disclosed herein. In some examples, aspects of the operations of 1525 may be performed by a sensor combination selection component 1240 as described with reference to FIG. 12.

Figure 16:
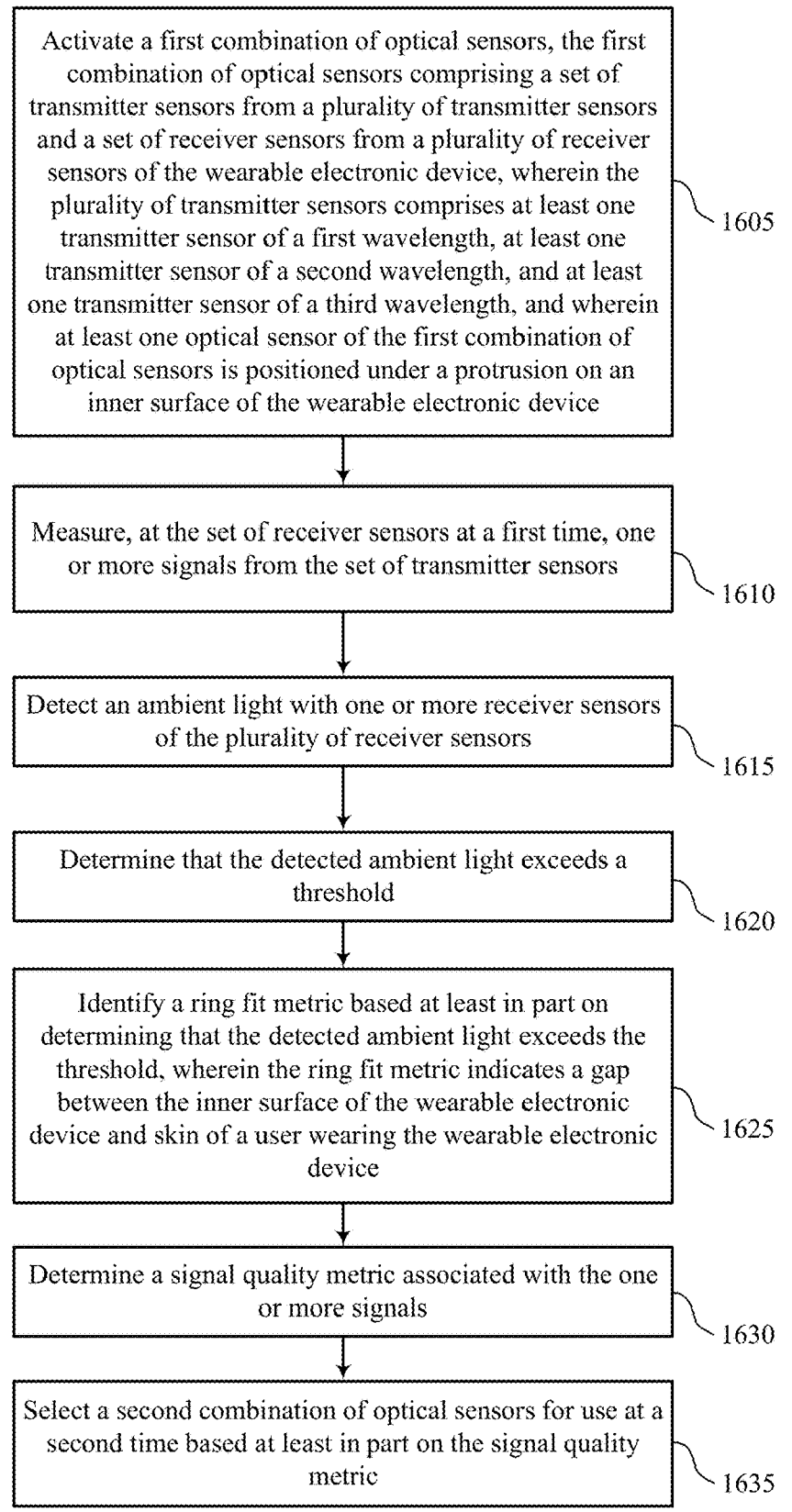

FIG. 16 shows a flowchart illustrating a method 1600 that supports a configurable PPG system in accordance with aspects of the present disclosure. The operations of the method 1600 may be implemented by a wearable device or its components as described herein. For example, the operations of the method 1600 may be performed by a wearable device as described with reference to FIGS. 1 through 13. In some examples, a wearable device may execute a set of instructions to control the functional elements of the wearable device to perform the described functions. Additionally or alternatively, the wearable device may perform aspects of the described functions using special-purpose hardware.

At 1605, the method may include activating a first combination of optical sensors, the first combination of optical sensors comprising a set of transmitter sensors from a plurality of transmitter sensors and a set of receiver sensors from a plurality of receiver sensors of the wearable electronic device, wherein the plurality of transmitter sensors comprises at least one transmitter sensor of a first wavelength, at least one transmitter sensor of a second wavelength, and at least one transmitter sensor of a third wavelength, and wherein at least one optical sensor of the first combination of optical sensors is positioned under a protrusion on an inner surface of the wearable electronic device. The operations of 1605 may be performed in accordance with examples as disclosed herein. In some examples, aspects of the operations of 1605 may be performed by a sensor activation component 1225 as described with reference to FIG. 12.

At 1610, the method may include measuring, at the set of receiver sensors at a first time, one or more signals from the set of transmitter sensors. The operations of 1610 may be performed in accordance with examples as disclosed herein. In some examples, aspects of the operations of 1610 may be performed by a signal measurement component 1230 as described with reference to FIG. 12.

At 1615, the method may include detecting an ambient light with one or more receiver sensors of the plurality of receiver sensors. The operations of 1615 may be performed in accordance with examples as disclosed herein. In some examples, aspects of the operations of 1615 may be performed by an ambient light component 1270 as described with reference to FIG. 12.

At 1620, the method may include determining that the detected ambient light exceeds a threshold. The operations of 1620 may be performed in accordance with examples as disclosed herein. In some examples, aspects of the operations of 1620 may be performed by an ambient light component 1270 as described with reference to FIG. 12.

At 1625, the method may include identifying a ring fit metric based at least in part on determining that the detected ambient light exceeds the threshold, wherein the ring fit metric indicates a gap between the inner surface of the wearable electronic device and skin of a user wearing the wearable electronic device. The operations of 1625 may be performed in accordance with examples as disclosed herein. In some examples, aspects of the operations of 1625 may be performed by a ring fit identification component 1275 as described with reference to FIG. 12.

At 1630, the method may include determining a signal quality metric associated with the one or more signals. The operations of 1630 may be performed in accordance with examples as disclosed herein. In some examples, aspects of the operations of 1630 may be performed by a signal quality component 1235 as described with reference to FIG. 12.

At 1635, the method may include selecting a second combination of optical sensors for use at a second time based at least in part on the signal quality metric. The operations of 1635 may be performed in accordance with examples as disclosed herein. In some examples, aspects of the operations of 1635 may be performed by a sensor combination selection component 1240 as described with reference to FIG. 12.

It should be noted that the methods described above describe possible implementations, and that the operations and the steps may be rearranged or otherwise modified and that other implementations are possible. Furthermore, aspects from two or more of the methods may be combined.

A method for measuring optical signals by a wearable electronic device is described. The method may include activating a first combination of optical sensors, the first combination of optical sensors comprising a set of transmitter sensors from a plurality of transmitter sensors and a set of receiver sensors from a plurality of receiver sensors of the wearable electronic device, where the plurality of transmitter sensors comprises at least one transmitter sensor of a first wavelength, at least one transmitter sensor of a second wavelength, and at least one transmitter sensor of a third wavelength, and where at least one optical sensor of the first combination of optical sensors is positioned under a protrusion on an inner surface of the wearable electronic device, measuring, at the set of receiver sensors at a first time, one or more signals from the set of transmitter sensors, determining a signal quality metric associated with the one or more signals, and selecting a second combination of optical sensors for use at a second time based at least in part on the signal quality metric.

An apparatus for measuring optical signals by a wearable electronic device is described. The apparatus may include a processor, memory coupled with the processor, and instructions stored in the memory. The instructions may be executable by the processor to cause the apparatus to activate a first combination of optical sensors, the first combination of optical sensors comprising a set of transmitter sensors from a plurality of transmitter sensors and a set of receiver sensors from a plurality of receiver sensors of the wearable electronic device, where the plurality of transmitter sensors comprises at least one transmitter sensor of a first wavelength, at least one transmitter sensor of a second wavelength, and at least one transmitter sensor of a third wavelength, and where at least one optical sensor of the first combination of optical sensors is positioned under a protrusion on an inner surface of the wearable electronic device, measure, at the set of receiver sensors at a first time, one or more signals from the set of transmitter sensors, determine a signal quality metric associated with the one or more signals, and select a second combination of optical sensors for use at a second time based at least in part on the signal quality metric.

Another apparatus for measuring optical signals by a wearable electronic device is described. The apparatus may include means for activating a first combination of optical sensors, the first combination of optical sensors comprising a set of transmitter sensors from a plurality of transmitter sensors and a set of receiver sensors from a plurality of receiver sensors of the wearable electronic device, where the plurality of transmitter sensors comprises at least one transmitter sensor of a first wavelength, at least one transmitter sensor of a second wavelength, and at least one transmitter sensor of a third wavelength, and where at least one optical sensor of the first combination of optical sensors is positioned under a protrusion on an inner surface of the wearable electronic device, means for measuring, at the set of receiver sensors at a first time, one or more signals from the set of transmitter sensors, means for determining a signal quality metric associated with the one or more signals, and means for selecting a second combination of optical sensors for use at a second time based at least in part on the signal quality metric.

A non-transitory computer-readable medium storing code for measuring optical signals by a wearable electronic device is described. The code may include instructions executable by a processor to activate a first combination of optical sensors, the first combination of optical sensors comprising a set of transmitter sensors from a plurality of transmitter sensors and a set of receiver sensors from a plurality of receiver sensors of the wearable electronic device, where the plurality of transmitter sensors comprises at least one transmitter sensor of a first wavelength, at least one transmitter sensor of a second wavelength, and at least one transmitter sensor of a third wavelength, and where at least one optical sensor of the first combination of optical sensors is positioned under a protrusion on an inner surface of the wearable electronic device, measure, at the set of receiver sensors at a first time, one or more signals from the set of transmitter sensors, determine a signal quality metric associated with the one or more signals, and select a second combination of optical sensors for use at a second time based at least in part on the signal quality metric.

In some examples of the method, apparatuses, and non-transitory computer-readable medium described herein, selecting the second combination of optical sensors may include operations, features, means, or instructions for selecting a second set of transmitter sensors, a second set of receiver sensors, or a combination thereof based at least in part on the signal quality metric.

In some examples of the method, apparatuses, and non-transitory computer-readable medium described herein, the second set of transmitter sensors and the second set of receiver sensors may be positioned around the wearable electronic device and selecting the second combination of optical sensors may be based at least in part on the positioning of the second set of transmitter sensors and the second set of receiver sensors.

In some examples of the method, apparatuses, and non-transitory computer-readable medium described herein, the wearable electronic device comprises a first photodiode and a second photodiode, the first photodiode and the second photodiode located under a first protrusion and a second protrusion, respectively, in the wearable electronic device.

In some examples of the method, apparatuses, and non-transitory computer-readable medium described herein, the at least one transmitter sensor of the first wavelength comprises a first green LED and a second green LED, the first green LED positioned to the right of the first photodiode and the second green LED positioned to the left of the second photodiode.

In some examples of the method, apparatuses, and non-transitory computer-readable medium described herein, the at least one transmitter sensor of the second wavelength comprises an infrared LED, the infrared LED positioned to the right of the first green LED.

In some examples of the method, apparatuses, and non-transitory computer-readable medium described herein, the at least one transmitter sensor of the third wavelength comprises a red LED, the red LED positioned to the left of the second green LED, the red LED and the infrared LED positioned next to one another.

In some examples of the method, apparatuses, and non-transitory computer-readable medium described herein, the infrared LED and the red LED may be positioned under a third protrusion in the wearable electronic device.

In some examples of the method, apparatuses, and non-transitory computer-readable medium described herein, selecting the second combination of optical sensors may include operations, features, means, or instructions for selecting a pair of optical sensors, the pair of optical sensors comprising at least one transmitter optical sensor and at least one receiver optical sensor.

In some examples of the method, apparatuses, and non-transitory computer-readable medium described herein, measuring the one or more signals may include operations, features, means, or instructions for measuring, by the set of receiver sensors, a PPG signal from the set of transmitter sensors.

In some examples of the method, apparatuses, and non-transitory computer-readable medium described herein, determining the signal quality metric may include operations, features, means, or instructions for determining an amplitude of the PPG signal, an amount of noise in the PPG signal, a form of the PPG signal, power consumption associated with determining the PPG signal, or a combination thereof.

Some examples of the method, apparatuses, and non-transitory computer-readable medium described herein may further include operations, features, means, or instructions for selecting a wavelength from a set of wavelengths based at least in part on a set of parameters for use in generating the one or more signals, where selecting the second combination of optical sensors may be based at least in part on the selected wavelength.

In some examples of the method, apparatuses, and non-transitory computer-readable medium described herein, selecting the second combination of optical sensors may include operations, features, means, or instructions for selecting between the at least one transmitter sensor of the first wavelength or the at least one transmitter sensor of the second wavelength.

In some examples of the method, apparatuses, and non-transitory computer-readable medium described herein, determining the signal quality metric may include operations, features, means, or instructions for determining a signal quality, a time of day, a motion of a user of the wearable electronic device, a temperature, a wavelength associated with the first set of optical sensors, or a combination thereof.

Some examples of the method, apparatuses, and non-transitory computer-readable medium described herein may further include operations, features, means, or instructions for updating a sampling rate associated with the first combination of optical sensors, the second combination of optical sensors, or both, based at least in part on the signal quality metric.

Some examples of the method, apparatuses, and non-transitory computer-readable medium described herein may further include operations, features, means, or instructions for updating a power output level associated with the first combination of optical sensors, the second combination of optical sensors, or both, based at least in part on the signal quality metric.

Some examples of the method, apparatuses, and non-transitory computer-readable medium described herein may further include operations, features, means, or instructions for updating sensor activation time associated with the first combination of optical sensors, the second combination of optical sensors, or both, based at least in part on the signal quality metric.

Some examples of the method, apparatuses, and non-transitory computer-readable medium described herein may further include operations, features, means, or instructions for detecting ambient light with one or more receiver sensors of the plurality of receiver sensors, determining that the detected ambient light exceeds a threshold, and identifying a ring fit metric based at least in part on determining that the detected ambient light exceeds the threshold, where the ring fit metric indicates a gap between the inner surface of the wearable electronic device and skin of a user wearing the wearable electronic device.

In some examples of the method, apparatuses, and non-transitory computer-readable medium described herein, and the method, apparatuses, and non-transitory computer-readable medium may include further operations, features, means, or instructions for activating the infrared LED that may be dedicated for finger wearing detection and determining whether the wearable electronic device may be being worn by a user based at least in part on whether the activated infrared LED that may be dedicated for finger wearing detection may be detected by one or more of the plurality of receiver sensors.

A wearable electronic device for measuring optical signals is described. The wearable electronic device may include a set of receiver sensors positioned on an inner surface of the wearable electronic device, the inner surface contacting a user of the wearable electronic device when the user is wearing the wearable electronic device, at least one receiver sensor of the set of receiver sensors positioned under a protrusion on the inner surface of the wearable electronic device. The wearable electronic device may include a first set of transmitter sensors positioned adjacent the first set of optical sensors on the inner surface, where the first set of transmitter sensors comprises one or more transmitter sensors of a first wavelength, and a second set of transmitter sensors positioned adjacent the second set of optical sensors on the inner surface, where the second set of transmitter sensors comprises at least one transmitter sensor of a second wavelength and at least one transmitter sensor of a third wavelength.

In some examples of the wearable electronic device, the first set of receiver sensors may further include at least two photodiodes, the first set of transmitter sensors comprises at least two green LEDs, and the second set of optical sensors comprises at least one infrared LED and at least one red LED.

In some examples of the wearable electronic device, the at least two photodiodes may further include a first photodiode and a second photodiode arranged with space between the first photodiode and the second photodiode.

In some examples of the wearable electronic device, the at least two green LEDs may further include a first green LED and a second green LED arranged in the space between the first photodiode and the second photodiode, the first green LED positioned to the right of the first photodiode and the second green LED positioned to the left of the second photodiode.

Some examples of the wearable electronic device may further include the at least one infrared LED positioned to the right of the first green LED and the at least one red LED positioned to the left of the second green LED, and the at least one infrared LED and the at least one red LED are positioned next to each other.

Some examples of the wearable electronic device may further include an additional infrared LED positioned to the left of the first photodiode, where the additional infrared LED may be positioned such that light emitted from the additional infrared LED may be directed towards the second photodiode.

In some examples of the wearable electronic device, the third set of optical sensors may be positioned under a protrusion on the inner surface of the wearable electronic device, the protrusion directed to the user of the wearable electronic device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device, comprising:
a ring-shaped housing comprising an inner curved surface and an outer curved surface, the inner curved surface configured to contact a tissue of a user when the wearable ring device is worn by the user;
a set of one or more receiver sensors positioned on or within the inner curved surface of the ring-shaped housing in at least a first radial position;
a first set of one or more transmitter sensors positioned on or within the inner curved surface of the ring-shaped housing in at least a second radial position, wherein the first set of one or more transmitter sensors are configured to emit light associated with a first wavelength;
a second set of one or more transmitter sensors positioned on or within the inner curved surface of the ring-shaped housing in at least a third radial position, wherein the second set of one or more transmitter sensors are configured to emit light associated with a second wavelength and a third wavelength; and
one or more processors communicatively coupled with the set of one or more receiver sensors, the first set of one or more transmitter sensors, and the second set of one or more transmitter sensors, wherein the one or more processors are configured to cause the wearable ring device to:
activate a first combination of optical sensors, the first combination of optical sensors comprising at least one receiver sensor from the set of one or more receiver sensors and at least one transmitter sensor from the first set of one or more transmitter sensors and the second set of one or more transmitter sensors;
measure, at a first time via the at least one receiver sensor of the first combination of optical sensors, one or more signals from the at least one transmitter sensor;
determine a signal quality metric associated with the one or more signals; and
select a combination of optical sensors for use at a second time based at least in part on the signal quality metric, the selected combination of optical sensors comprising the first combination of optical sensors or a second combination of optical sensors.

2. The wearable ring device of claim 1, wherein at least one receiver sensor of the set of one or more receiver sensors, at least one transmitter sensor of the first set of one or more transmitter sensors, at least one transmitter sensor of the second set of one or more transmitter sensors, or any combination thereof, is positioned under a protrusion extending from the inner curved surface of the wearable ring device.

3. The wearable ring device of claim 1, further comprising:
a first protrusion extending from the inner curved surface of the wearable ring device at the first radial position; and
a second protrusion extending from the inner curved surface of the wearable ring device at the second radial position or the third radial position.

4. The wearable ring device of claim 1, further comprising:
a first protrusion extending from the inner curved surface of the wearable ring device at the second radial position; and
a second protrusion extending from the inner curved surface of the wearable ring device at the third radial position.

5. The wearable ring device of claim 1, further comprising:
a protrusion extending from the inner curved surface of the wearable ring device, wherein the protrusion spans the first radial position and the second radial position such that at least one receiver sensor of the set of one or more receiver sensors and at least one transmitter sensor of the first set of one or more transmitter sensors are positioned beneath the protrusion.

6. The wearable ring device of claim 1, wherein the first set of one or more transmitter sensors comprises a first transmitter sensor in the second radial position and a second transmitter sensor in a fourth radial position, the first and second transmitter sensors configured to emit light associated with the first wavelength,
and wherein the one or more processors are further configured to cause the wearable ring device to:
activate the first combination of optical sensors, the first combination of optical sensors comprising the first transmitter sensor and at least one receiver sensor from the set of one or more receiver sensors; and
select the second combination of optical sensors for use at the second time based at least in part on the signal quality metric, the second combination of optical sensors comprising the second transmitter sensor and the at least one receiver sensor from the set of one or more receiver sensors, an additional receiver sensor from the set of one or more receiver sensors, or both.

7. The wearable ring device of claim 1,
wherein the one or more processors are further configured to cause the wearable ring device to:
activate the first combination of optical sensors, the first set of one or more transmitter sensors comprising at least one transmitter sensor configured to emit light associated with the first wavelength, at least one transmitter sensor configured to emit light associated with the second wavelength, and at least one transmitter sensor configured to emit light associated with the third wavelength; and
select the second combination of optical sensors for use at the second time based at least in part on the signal quality metric.

8. The wearable ring device of claim 1, wherein the set of one or more receiver sensors comprises at least two photodiodes, the first set of one or more transmitter sensors comprises at least two green LEDs, and the second set of one or more transmitter sensors comprises at least one infrared LED and at least one red LED.

9. The wearable ring device of claim 1, wherein the set of one or more receiver sensors comprises a first receiver sensor at the first radial position, and a second receiver sensor at a fourth radial position.

10. A method for measuring optical signals by a wearable ring device, comprising:
activating a first combination of optical sensors, the first combination of optical sensors comprising a set of transmitter sensors from a plurality of transmitter sensors and a set of receiver sensors from a plurality of receiver sensors of the wearable ring device, wherein the plurality of transmitter sensors comprise at least one transmitter sensor of a first wavelength, at least one transmitter sensor of a second wavelength, and at least one transmitter sensor of a third wavelength, wherein the plurality of transmitter sensors are positioned at two or more radial positions along an inner curved surface of the wearable ring device, and wherein the plurality of receiver sensors of the wearable ring device are positioned at least at an additional radial position along the inner curved surface of the wearable ring device;
measuring, at the set of receiver sensors at a first time, one or more signals from the set of transmitter sensors;
determining a signal quality metric associated with the one or more signals; and
selecting a second combination of optical sensors for use at a second time based at least in part on the signal quality metric.

11. The method of claim 10, wherein at least one optical sensor of the first combination of optical sensors is positioned under a protrusion extending from the inner curved surface of the wearable ring device.

12. The method of claim 10, wherein selecting the second combination of optical sensors comprises:
selecting a second set of transmitter sensors, a second set of receiver sensors, or a combination thereof, based at least in part on the signal quality metric.

13. The method of claim 10, wherein the plurality of receiver sensors comprise a first photodiode and a second photodiode, wherein the first photodiode and the second photodiode are positioned beneath a first protrusion and a second protrusion, respectively, extending from the inner curved surface of the wearable ring device.

14. The method of claim 13, wherein the first photodiode and the second photodiode are positioned at a first radial position and a second radial position, respectively, along the inner curved surface of the wearable ring device, wherein the at least one transmitter sensor of the first wavelength comprises a first green LED and a second green LED positioned at a third radial position and a fourth radial position, respectively, wherein the first and second radial positions are located between the third and fourth radial positions.

15. The method of claim 13, wherein the first protrusion associated with the first photodiode and the second protrusion associated with the second photodiode are positioned at a first radial position and a second radial position, respectively, wherein the at least one transmitter sensor of the second wavelength comprises an infrared LED, and wherein the at least one transmitter sensor of the third wavelength comprises a red LED, wherein the infrared LED and the red LED are positioned adjacent to one another at a third radial position.

16. The method of claim 15, wherein the infrared LED and the red LED are positioned beneath a third protrusion extending from the inner curved surface of the wearable ring device at the third radial position.

17. The method of claim 10, further comprising:
updating a sampling rate, a power output level, a sensor activation time, or any combination thereof, associated with the first combination of optical sensors, the second combination of optical sensors, or both, based at least in part on the signal quality metric.

18. The method of claim 10, further comprising:
detecting an ambient light level with one or more receiver sensors of the plurality of receiver sensors;
determining that the detected ambient light level exceeds a threshold; and
identifying a ring fit metric based at least in part on determining that the detected ambient light level exceeds the threshold, wherein the ring fit metric is associated with a level of contact between the inner curved surface of the wearable ring device and skin of a user wearing the wearable ring device.

19. An apparatus for measuring optical signals by a wearable ring device, comprising:
at least one processor;
at least one memory coupled with the at least one processor; and
instructions stored in the at least one memory and executable by the at least one processor to cause the apparatus to:
activate a first combination of optical sensors, the first combination of optical sensors comprising a set of transmitter sensors from a plurality of transmitter sensors and a set of receiver sensors from a plurality of receiver sensors of the wearable ring device, wherein the plurality of transmitter sensors comprise at least one transmitter sensor of a first wavelength, at least one transmitter sensor of a second wavelength, and at least one transmitter sensor of a third wavelength, wherein the plurality of transmitter sensors are positioned at two or more radial positions along an inner curved surface of the wearable ring device, and wherein the plurality of receiver sensors of the wearable ring device are positioned at least at an additional radial position along the inner curved surface of the wearable ring device;
measure, at the set of receiver sensors at a first time, one or more signals from the set of transmitter sensors;
determine a signal quality metric associated with the one or more signals; and
select a second combination of optical sensors for use at a second time based at least in part on the signal quality metric.

20. The apparatus of claim 19, wherein at least one optical sensor of the first combination of optical sensors is positioned under a protrusion extending from the inner curved surface of the wearable ring device.

\* \* \* \* \*